United States Patent
Nagamine

(10) Patent No.: US 7,374,913 B2
(45) Date of Patent: *May 20, 2008

(54) METHOD FOR SYNTHESIZING POLYNUCLEOTIDES

(75) Inventor: Kentaro Nagamine, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 521 days.

This patent is subject to a terminal disclaimer.

(21) Appl. No.: 10/380,930

(22) PCT Filed: Sep. 19, 2001

(86) PCT No.: PCT/JP01/08142

§ 371 (c)(1), (2), (4) Date: Jun. 18, 2003

(87) PCT Pub. No.: WO02/24902

PCT Pub. Date: Mar. 28, 2002

(65) Prior Publication Data

US 2004/0038253 A1 Feb. 26, 2004

(30) Foreign Application Priority Data

Sep. 19, 2000 (JP) ............................. 2000-283862

(51) Int. Cl.
- C12N 15/09 (2006.01)
- C12N 15/10 (2006.01)
- C12Q 1/68 (2006.01)

(52) U.S. Cl. .......................................... 435/91.2; 435/6

(58) Field of Classification Search ...................... None
See application file for complete search history.

(56) References Cited

U.S. PATENT DOCUMENTS

2003/0207292 A1 * 11/2003 Notomi et al. .................. 435/6

FOREIGN PATENT DOCUMENTS

| EP | 0 971 039 A2 | 1/2000 |
| EP | 1 020 534 A1 | 7/2000 |
| EP | 1 231 281 A1 | 8/2002 |
| JP | WO00/28082 * | 5/2000 |
| JP | 1020534 A1 * | 7/2000 |
| WO | WO 00/28082 | 5/2000 |
| WO | WO 01/34790 A1 | 5/2001 |
| WO | WO 01/34838 A1 | 5/2001 |

OTHER PUBLICATIONS

Notomi et al. "Loop-mediated isothermal amplification of DNA", Nucleic Acids Research, 2000, vol. 28, No. 12, p. i-vii.*
Notomi et al., "Loop-Mediated Isothermal Amplification of DNA," Nucleic Acids Research 28(12):e63 i-vii.
Notomi et al., "Loop-Mediated Isothermal Amplification of DNA," Nucleic Acids Research 28(12):e63 i-vii, 2000.

* cited by examiner

Primary Examiner—Gary Benzion
Assistant Examiner—Stephanie K. Mummert
(74) Attorney, Agent, or Firm—Nixon Peabody LLP

(57) ABSTRACT

The present invention realized isothermal and rapid polynucleotide synthesis by using as templates polynucleotides having a structure capable of forming loops, and combining a plurality of primers capable of providing a starting point for complementary strand synthesis to such loops. If the LAMP method is applied, all reactions can be carried out isothermally and rapidly since the template polynucleotides themselves can also be synthesized by an isothermal reaction.

18 Claims, 17 Drawing Sheets

FIG. 4

```
GGCTTGGCTCTGCTAACACGTTGCTCATAGGAGATATGGTAGAGCCG
      F3                                F2
CAGACACGTCGTATGCAGGAACGTGCTGCGGCTGGCTGGTGAACTTC
←─────────────────             F1
CGATAGTGCGGGTGTTGAATGATTTCCAGTTGCTACCGATTTTACAT

ATTTTTTGCATGAGAGAATTTGTACCACCTCCCACCGACCATCTATC
                        R1                ─────
ACTGTACGCCACTGTCCCTAGGACTGCTATGTGCCGGAGCGGACATT
─────────→
         R2                               R3
ACAAACGTCC
```

METHOD FOR SYNTHESIZING POLYNUCLEOTIDES

This application is a national stage application under 35 USC 371 of PCT/JP01/08142 filed Sep. 19, 2001, which claims the priority benefit of Japanese Application No. 2000-283862 filed Sep. 19, 2000.

TECHNICAL FIELD

The present invention relates to a method for synthesizing polynucleotides.

BACKGROUND ART

Template-dependent nucleic acid synthesis methods using the Polymerase Chain Reaction (PCR) method have served as a major driving force for research in bioscience fields in recent years. The PCR method has made it possible to exponentially amplify nucleic acids composed of a nucleotide sequence complementary to a template by using a small amount of double-stranded nucleic acid as template. PCR is currently widely used as a tool for gene cloning and detection. In the PCR method, one set of primers comprising nucleotide sequences complementary to both ends of a target nucleotide sequence is used. One of the primers is designed to anneal to the elongation product generated by the other primer. In this manner, a synthesis reaction progresses in which annealing to a mutual elongation product and complementary strand synthesis are repeated, enabling exponential amplification to be achieved.

In the PCR method, complex temperature control is essential. A special reaction apparatus must be used to accommodate this complex temperature control. Thus, it is difficult to perform PCR at hospital bedsides or outdoors. In addition, improvement of reaction specificity has been an important problem for known complementary strand synthesis reactions. For example, in the PCR method, when a complementary strand synthesis product is used as a new template, the region to which the primer anneals is not a nucleotide sequence derived from the sample in the strict sense, but rather is merely a copy of the nucleotide sequence of the primer. Thus, it is typically difficult to recognize slight differences in nucleotide sequences using a PCR primer.

As one method for solving these problems, the LAMP method was invented (Loop-mediated isothermal amplification) (Nucleic Acid Res. 2000, Vol. 28, No. 12 e63, WO 00/28082). The LAMP method makes it possible to anneal to a template polynucleotide its own 3'-end to serve as a starting point for complementary strand synthesis, while also enabling an isothermal complementary strand synthesis reaction by combining a primer that is annealed to the loop formed at this time. In addition, in the LAMP method, since the 3'-end anneals to a region derived from the sample, a nucleotide sequence checking mechanism functions repeatedly. As a result, it has become possible to identify even slight differences in nucleotide sequences.

When detecting a target nucleotide sequence based on a complementary strand synthesis reaction such as LAMP or PCR, there is a close relationship between the time required for the reaction and detection sensitivity. In other words, allowing the reaction to proceed for as long a time as possible until the reaction reaches a plateau is a condition for achieving high detection sensitivity. In the case of known complementary strand synthesis reactions like LAMP and PCR, the reaction reaches a plateau in about 1 hour. In other words, it may be said that a reaction time of about 1 hour is required in order to obtain maximum sensitivity. Although a reaction time of 1 hour is not that long, it would be even more useful if an even shorter reaction time can be realized without sacrificing detection sensitivity or procedural ease.

Following the identification of the genome draft, science is entering a post-genome era. There is a growing need for analyzing single nucleotide polymorphisms (SNPs) and gene function as well as gene diagnosis based on the results of those analyses. Thus, the development of a technology that enables gene nucleotide sequences to be analyzed more accurately and rapidly is becoming an important issue not only in terms of rapidly carrying out functional analysis, but also with respect to practical application of the results of gene function analysis in actual clinical settings.

DISCLOSURE OF THE INVENTION

The objective of the present invention is to provide a method that can rapidly carry out a complementary strand synthesis reaction using a polynucleotide as template.

The inventor conducted extensive research on reaction conditions for complementary strand synthesis to solve the above problems. As a result, it was found that the combination of primers used for complementary strand synthesis and the 3'-end serving as the starting point for complementary strand synthesis was intimately related to the reaction rate of complementary strand synthesis. Moreover, it was revealed that the reaction efficiency of complementary strand synthesis can be improved by combining a template polynucleotide having a specific structure with a primer capable of providing the starting point for complementary strand synthesis at a specific location of this polynucleotide, thereby leading to the completion of the present invention. Namely, the present invention relates to the following polynucleotide synthesis method and the application thereof.

[1] A method for synthesizing a polynucleotide comprising the steps of mixing the following elements 1 to 5, and incubating under conditions that allow template-dependent complementary strand synthesis using the DNA polymerase in 4:

1: a template polynucleotide that:
 (a) has a target nucleotide sequence comprising at least one set of complementary nucleotide sequences,
 (b) forms a loop capable of base pairing when the complementary nucleotide sequence of (a) hybridizes,
 (c) forms a loop by the annealing of its 3'-end to itself, and
 (d) whose 3'-end annealed to itself can be a starting point for complementary strand synthesis using itself as template;
2: at least two types of primers providing starting points for complementary strand synthesis at different locations on the template polynucleotide loop;
3: at least one type of primer providing a starting point for complementary strand synthesis at a location different from the primers of 2 in a loop formed by template polynucleotide and/or an elongation product produced by the annealing of the primers of 2 to the template polynucleotide;
4: a DNA polymerase catalyzing complementary strand synthesis accompanying strand displacement; and,
5: a substrate for complementary strand synthesis.

[2] The method of [1], wherein said template polynucleotide has on its 5'-end a nucleotide sequence complementary to an arbitrary region of its own nucleotide sequence.

[3] The method of [2], wherein said template polynucleotide is produced by the following steps of:
 a) annealing a first primer to a target nucleotide sequence, and conducting a complementary strand synthesis. reaction using this as a starting point, wherein said first primer (i) can provide at the 3'-end a starting point for complementary strand synthesis to a region that defines the 3'-side of one of the strands that compose the target nucleotide sequence, and (ii) has on its 5'-side a nucleotide sequence complementary to an arbitrary region of a complementary strand synthesis reaction product that uses this primer as a starting point;

b) placing, in a condition that allows base pairing, the region to where a second primer is to anneal in the elongation product of the first primer synthesized in step a), wherein said second primer (i) has on its 3'-end a nucleotide sequence providing a starting point for complementary strand synthesis to a region that defines the 3'-side of a target nucleotide sequence in the elongation product that uses the first primer as a starting point, and (ii) has on its 5'-side a nucleotide sequence that is complementary to an arbitrary region of a complementary strand synthesis reaction product that uses this primer as an starting point;

c) annealing said second primer to the region that can form base pairing in step b), and carrying out complementary strand synthesis using this as a starting point; and, d) annealing the 3'-end of the elongation product of the second primer synthesized in step c) to itself, and carrying out complementary strand synthesis using itself as template.

[4] The method of [3], wherein the two types of primers are a first primer and a second primer, and at least one type of the primers is a loop primer providing, between a region derived from each primer in the elongation product of the first primer or second primer and the arbitrary region with respect to each primer, a starting point for complementary strand synthesis.

[5] The method of [4], wherein said loop primer is (i) a first loop primer providing, between a region derived from the first primer in the elongation product of the first primer and the arbitrary region with respect to the first primer, a starting point for complementary strand synthesis, and (ii) a second loop primer providing, between a region derived from the second primer in the elongation product of the second primer and the arbitrary region with respect to the second primer, a starting point for complementary strand synthesis.

[6] The method of [4], wherein said loop primer further comprises on its 5'-end a nucleotide sequence complementary to the arbitrary region.

[7] The method of [3], wherein each product of the first primer or second primer is converted to a single strand by displacing the elongation product of the first primer and/or second primer according to complementary strand synthesis from an outer primer that provides a starting point for complementary strand synthesis to the 3'-side of a template with respect to the first primer or second primer in step b) and/or step c).

[8] The method of [3], wherein the target nucleotide sequence is present as a double-stranded polynucleotide in step a), and the region to which the first primer is annealed is made to form base pair bonds according to a complementary strand synthesis reaction using the arbitrary primer as a starting point.

[9] The method of [8], wherein step a) is carried out in the presence of a melting temperature regulator.

[10] The method of [9], wherein the melting temperature regulator is at least one compound selected from the group consisting of betaine, proline, dimethylsulfoxide, and trimethylamine N-oxide.

[11] A method for amplifying a template polynucleotide, comprising the step of repeating complementary strand synthesis using the template polynucleotide as template according to the method of [1] or [5], and also carrying out another polynucleotide synthesis reaction according to the method of [1] or [5] using the elongation product resulting from the synthesis reaction as a new template polynucleotide.

[12] A method for detecting a target nucleotide sequence in a sample, comprising the step of carrying out the amplification method of [11], and correlating the production of the amplification reaction product with the presence of a target nucleotide sequence.

[13] The method of [12], wherein the method of [11] is carried out in the presence of a polynucleotide detecting agent, and whether or not an amplification reaction product is produced is observed based on a signal change of the detecting agent.

[14] A method for detecting a mutation in a target nucleotide sequence according to the detection method of [12], the method comprising the steps of (i) blocking at least one of the complementary strand synthesis reactions selected from the complementary strand synthesis reactions composing the amplification method, when the target nucleotide sequence is not the predicted nucleotide sequence, and (ii) observing the inhibition of the amplification reaction.

[15] The method of [14] that uses the following first primer and second primer, wherein at least either the first primer or second primer comprises a checking sequence on its 5'-side, wherein, a checking sequence refers to a nucleotide sequence in which (i) when a nucleotide sequence that composes a specific region is not the predicted nucleotide sequence, a mismatch occurs at the time when the 3'-end of the complementary strand synthesized using the checking sequence as template anneals to the target nucleotide sequence, or its complementary strand, and (ii) a complementary strand synthesis reaction that starts by using the 3'-end as a starting point is inhibited by this mismatch, the first primer (i) can provide at its 3'-end a starting point for complementary strand synthesis to a region that defines the 3'-side of one of the strands that composes a target nucleotide sequence, and (ii) has on its 5'-side a nucleotide sequence that is complementary to the arbitrary region of the complementary strand synthesis reaction product that uses this primer as a starting point, and the second primer (i) has a nucleotide sequence on its 3'-end that provides a starting point for complementary strand synthesis to a region that defines the 3'-side of a target nucleotide sequence in an elongation product that uses the first primer as a starting point, and (ii) has on its 5'-side a nucleotide sequence that is complementary to the arbitrary region of the complementary strand synthesis reaction product that uses this primer as a starting point.

[16] The method of [15], wherein when the nucleotide sequence that composes the specific region is not the predicted nucleotide sequence, a mismatch occurs in the 2nd to 4th nucleotides from the 3'-end of the complementary strand at the time when the complementary strand synthesized by using a checking sequence as template anneals to the target nucleotide sequence, or its complementary strand.

[17] The method of [15] that uses the following first loop primer and/or second loop primer as loop primers; provided that, when the loop primer comprises on its 5'-side a nucleotide that is complementary to the arbitrary region arranged on the 5'-side of the primer, or when the nucleotide sequence arranged on the 5'-side of the primer is a checking sequence, a sequence in which the nucleotide for providing the mismatch in the checking sequence differs from the checking sequence is arranged on the 5'-side of the loop primer:

first loop primer: provides, between a region derived from a first primer in an elongation product of the first primer and the arbitrary region with respect to the first primer, a starting point for complementary strand synthesis;

second loop primer: provides, between a region derived from a second primer in an elongation product of the second primer and the arbitrary region with respect to the second primer, a starting point for complementary strand synthesis.

[18] The method of [17], wherein, when the nucleotide sequence that composes the specific region is not the predicted nucleotide sequence, a mismatch occurs in the 2nd to 4th nucleotides from the 3'-end of the complementary strand at the time when the complementary strand synthesized using a checking sequence as a template anneals to the target nucleotide sequence, or its complementary strand, and wherein, the nucleotide sequence arranged on the 5'-side of the first loop primer and/or second loop primer differs in the nucleotide that causes the mismatch in the checking sequence.

[19] A kit for amplifying a target nucleotide sequence comprising:

a) a first primer that (i) can provide at its 3'-end a starting point for complementary strand synthesis to a region that defines the 3'-side of one of the strands that compose the target nucleotide sequence, and (ii) has on its 5'-side a nucleotide sequence that is complementary to the arbitrary region of a complementary strand synthesis reaction product that uses this primer as an starting point;

b) a second primer that has (i) on its 3'-end a nucleotide sequence that provides a starting point for complementary strand synthesis to a region that defines the 3'-side of a target nucleotide sequence in an elongation product that uses the first primer as an starting point, and (ii) on its 5'-side a nucleotide sequence that is complementary to the arbitrary region of a complementary strand synthesis reaction product that uses this primer as a starting point;

c) a first loop primer that provides, between a region derived from the first primer in an elongation product of the first primer and the arbitrary region with respect to the first primer, a starting point for complementary strand synthesis;

d) a second loop primer that provides, between a region derived from the second primer in an elongation product of the second primer and the arbitrary region with respect to the second primer, a starting point for complementary strand synthesis;

e) a DNA polymerase catalyzing complementary strand synthesis accompanying strand displacement; and, f) a substrate for complementary strand synthesis.

[20] The kit of [19] that further comprises:

g) an outer primer that can provide a starting point for complementary strand synthesis to the 3'-side of a template of the first primer and/or second primer.

[21] The kit of [19], wherein the first primer and/or second primer comprise a checking sequence on the 5'-side.

[22] The kit of [19] comprising the following first loop primer and/or second loop primer as a loop primer; provided that, when the loop primer comprises on its 5'-side a nucleotide sequence that is complementary to the arbitrary region arranged on the 5'-side of the primer, or when the nucleotide sequence arranged on the 5'-side of the primer is a checking sequence, the nucleotide for providing the mismatch in the checking sequence arranges a sequence that differs from the checking sequence on the 5'-side of the loop primer:

first loop primer: provides, between a region derived from the first primer in an elongation product of the first primer and the arbitrary region with respect to the first primer, a starting point for complementary strand synthesis; and, second loop primer: provides, between a region derived from the second primer in an elongation product of the second primer, and the arbitrary region with respect to the second primer, a starting point for complementary strand synthesis.

[23] A method for amplifying a polynucleotide comprising the steps of mixing the following elements a) through g), and incubating under conditions that enable a complementary strand synthesis reaction accompanying strand displacement:

a) a first primer that (i) can provide at its. 3'-end a starting point for complementary strand synthesis to a region that defines the 3'-side of one of the strands that compose a target nucleotide sequence, and (ii) has on its 5'-side a nucleotide sequence that is complementary to the arbitrary region of a complementary strand synthesis reaction product that uses this primer as a starting point;

b) a second primer that has (i) on its 3'-end a nucleotide sequence that provides a starting point for complementary strand synthesis to a region that defines the 3'-side of a target nucleotide sequence in an elongation product that uses the first primer as a starting point, and (ii) on its 5'-side a nucleotide sequence that is complementary to the arbitrary region of a complementary strand synthesis reaction product that uses this primer as a starting point;

c) a first loop primer that can provide, between a region derived from the first primer in an elongation product of the first primer and the arbitrary region with respect to the first primer, a starting point for complementary strand synthesis;

d) a second loop primer that can provide, between a region derived from the second primer in an elongation product of the second primer and the arbitrary region with respect to the second primer, a starting point for complementary strand synthesis;

e) a DNA polymerase catalyzing complementary strand synthesis accompanying strand displacement;

f) a substrate for complementary strand synthesis; and, g) a test polynucleotide comprising a target nucleotide sequence.

[24] The method of [23] that further comprises:

h) an outer primer that provides a starting point for complementary strand synthesis to the 3'-side of a template with respect to the region in which the 3'-end of the first primer and/or second primer anneals to the target nucleotide sequence.

[25] A method for determining whether a specific nucleotide in a target nucleotide sequence is the first nucleotide or the second nucleotide, comprising the step of mixing the following elements a) through d), and incubating under conditions that enable a complementary strand synthesis reaction accompanying strand displacement, wherein formation rate and/or formed amount of the amplification product is measured by any one of the primer sets in a) selected from the group consisting of:

a)

(1): first nucleotide inner primer pair and first nucleotide loop primer pair (2): first nucleotide inner primer pair and second nucleotide loop primer pair (3): second nucleotide inner primer pair and first nucleotide loop primer pair, and (4): second nucleotide inner primer pair and second nucleotide loop primer pair;

wherein, the first nucleotide inner primer pair and the second nucleotide inner primer pair are both primer pairs consisting of the next first inner primer and second inner primer, and in the first nucleotide primer pair, a complementary strand synthesis reaction using as the starting point the 3'-end of the complementary strand synthesized using the 5'-sides of the first inner primer and second inner primer as a template is not inhibited when the specific nucleotide in the target nucleotide sequence is the first nucleotide, but is inhibited when it is the second nucleotide;

in the second nucleotide inner primer pair, a complementary strand synthesis using as the starting point the 3'-end of a complementary strand synthesized using the 5'-sides of the first inner primer and second inner primer as a template is not inhibited when the specific nucleotide in the target nucleotide sequence is the second nucleotide, but is inhibited when it is the first nucleotide;

the first inner primer has (i) on its 3'-end a nucleotide sequence that provides a starting point for complementary strand synthesis to a region that defines the 3'-side of one of the strands that compose a target nucleotide sequence, and (ii) on the 5'-side a nucleotide sequence that is complementary to the arbitrary, region of a complementary strand synthesis reaction product that uses this inner primer as an starting point;

the second inner primer has (i) on its 3'-end a nucleotide sequence that provides a starting point for complementary strand synthesis to a region that defines the 3'-side of a target nucleotide sequence in an elongation product that uses the first inner primer as an starting point, and (ii) on the 5'-side a nucleotide sequence that is complementary to the arbitrary region of a complementary strand synthesis reaction product that uses this inner primer as an starting point;

the first nucleotide loop primer pair and the second nucleotide loop primer pair are both pairs consisting of the next first loop primer and second loop primer, and in the first nucleotide loop primer pair, a complementary strand synthesis reaction using as the starting point the 3'-end of the complementary strand synthesized using the 5'-sides of the first loop primer and second loop primer as template is not inhibited when the specific nucleotide in the target nucleotide sequence is the first nucleotide, but is inhibited when it is the second nucleotide;

in the second nucleotide inner primer pair, a complementary strand synthesis reaction using as the starting point the 3'-end of a complementary strand synthesized using the 5'-sides of the first loop primer and second loop primer as a template is not inhibited when the specific nucleotide in the target nucleotide sequence is the second nucleotide, but is inhibited when it is the first nucleotide;

the first loop primer provides, between a region derived from the first inner primer in an elongation product of the first inner primer and the arbitrary region with respect to the first inner primer, a starting point for complementary strand synthesis, and the second loop primer provides, between a region derived from the second inner primer in an elongation product of the second inner primer and the arbitrary region with respect to the second inner primer, a starting point for complementary strand synthesis;

b) a DNA polymerase catalyzing complementary strand synthesis accompanying strand displacement;

c) a substrate for complementary strand synthesis; and d) a test polynucleotide comprising a target nucleotide sequence.

[26] The method of [25] that further comprises:

e) an outer primer that provides a staring point for complementary strand synthesis to the 3'-side of a template with respect to the region in which the 3'-end of the first primer and/or second primer anneals to the target nucleotide sequence.

The polynucleotides used in the present invention may be DNA, RNA, or chimeric molecules thereof. The polynucleotides may be natural nucleic acids, as well as artificially synthesized nucleic acids. Further, nucleotide derivatives having partially or completely artificial structures are also included in the polynucleotides of the present invention, so long as they can form base pairs and if necessary can be used as a template in complementary strand synthesis. Examples of such molecules include PNA in which the backbone is formed by peptide bonds. There is no limitation on the number of nucleotides in the polynucleotide of the present invention. The term polynucleotide is equivalent to the term nucleic acid. On the other hand, the term oligonucleotide as used herein especially refers to polynucleotides with a smaller number of nucleotides among polynucleotides. Typically, the term oligonucleotide refers to polynucleotides containing 2 to 100 nucleotide residues, more typically about 2 to 50 nucleotide residues, but is not limited thereto.

The term "target nucleotide sequence" of the present invention refers to the nucleotide sequence of the polynucleotide to be synthesized. In general, the nucleotide sequence of a polynucleotide is described from the 5'-side to the 3'-side of the sense strand. Further, the target nucleotide sequence of the present invention includes not only the sense strand, but also the nucleotide sequence of the complementary strand thereof, i.e. the antisense strand. More specifically, the term "target nucleotide sequence" refers to at least either the nucleotide sequence to be synthesized or the complementary strand thereof. Furthermore, the present invention provides a method that enables not only polynucleotide synthesis, but amplification as well. In the case of carrying out polynucleotide amplification based on the present invention, the nucleotide sequence to be amplified is referred to as the target nucleotide sequence. The target nucleotide sequence may be the arbitrary consecutive nucleotide sequence selected from within a long polynucleotide, or the full-length of a single-stranded or cyclic polynucleotide.

Furthermore, synthesis refers to the act of increasing a single target nucleotide sequence by at least two folds or more. On the other hand, when a continuously new target nucleotide sequence is synthesized based on the synthesized target nucleotide sequence, this is specifically referred to as amplification. Amplification can also be referred to as continuous synthesis.

Moreover, in the present invention, the provision of a starting point for complementary strand synthesis refers to the hybridization of the 3'-end of a polynucleotide that functions as a primer required for complementary strand synthesis to a polynucleotide that serves as a template. When a starting point for complementary strand synthesis is provided at a specific region, this means that the polynucleotide is hybridized so that the 3'-end that is to serve as the starting point for complementary strand synthesis is located at an arbitrary location within the region. At this time, the portion of the nucleotide sequence required for hybridization may also be arranged outside that region provided the 3'-end is located in the target region.

On the other hand, the above-mentioned DNA polymerase catalyzes a complementary strand synthesis reaction that uses as a starting point each of the primers annealed to the above template polynucleotide as well as its own 3'-end under conditions that enable template-dependent complementary strand synthesis. In the present invention, "conditions that enable template-dependent complementary strand synthesis" refer to a reaction in which a new polynucleotide chain comprising a nucleotide sequence complementary to the nucleotide sequence of the template polynucleotide is synthesized by using as a starting point the 3'-end of the polynucleotide annealed to the template. In the present invention, a new polynucleotide chain may also be a molecule that differs from the template or a molecule that is the same as the template. For example, a new polynucleotide chain produced by a complementary strand synthesis reaction that proceeds by annealing the 3'-end of a polynucleotide to itself, is the same molecule as the template polynucleotide. In the present invention, conditions that enable template-dependent complementary strand synthesis may also simply be referred to as conditions that enable complementary strand synthesis.

Such reactions can normally be conducted in a buffer that provides the optimum reaction conditions for the DNA polymerase. A protective agent that protects the activity of the DNA polymerase, inorganic salts required to maintain the activity and so forth may also be present together in the buffer. Such reaction conditions can be suitably selected by a person with ordinary skill in the art according to the DNA polymerase.

In the present invention, the terms "3'-end" and "5'-end" do not refer to the nucleotide of either terminus, but rather, refer to a region located at the terminus that includes the single end nucleotide. More specifically, 500 nucleotides, preferably 100 nucleotides, or at least 20 nucleotides from either terminus are included in the terms "3'-end" and "5'-end". In contrast, in order to indicate a single end nucleotide or a nucleotide at a specific location present in the vicinity of a terminus, the numerical value of the location thereof is specified.

The target nucleotide sequence of the present invention comprises at least a pair of complementary nucleotide sequences. The terms "identical" and "complementary" as used herein encompass cases that are not completely identical and not completely complementary. More specifically, a sequence identical to a certain sequence also includes a sequence complementary to a nucleotide sequence that can anneal to the certain sequence. On the ocher hand, a complimentary sequence refers to a sequence that anneals under stringent conditions, and provides a 3'-end as the starting point for complementary strand synthesis. More specifically, a nucleotide sequence that has an identity of typically 50% to 100%, normally 70% to 100%, and preferably 80% to 100% to a certain nucleotide sequence can be mentioned as being a sequence that is substantially identical. Identity can be determined based on known algorithms such as BLAST.

A template polynucleotide of the present invention is capable of forming a loop when the above complementary nucleotide sequence hybridizes. After the complementary nucleotide sequence is hybridized, it is difficult for new base pair bonds to occur under conditions under which base pairing is kept stable. On the other hand, a loop is able to form new base pair bonds with a different polynucleotide composed of a nucleotide sequence complementary to the nucleotide sequence that composes this loop. The nucleotide sequence that composes the loop is arbitrary.

The term "hybridize" used in the present invention refers to the bonding of a polynucleotide comprising a complementary nucleotide sequence by base pairing. The polynucleotide that undergoes base pairing may be a different molecule or the same molecule. If hybridization that has occurred between different molecules is terminated, dissociation into a plurality of polynucleotide molecules will occur. On the other hand, a polynucleotide that has hybridized on the same molecule remains as one polynucleotide even if the base pair bonds are dissolved. In the present invention, the term "anneal" is also used. There are cases in particular in which the term anneal is used when a polynucleotide hybridizes to a polynucleotide comprising a complementary nucleotide sequence, and provides a 3'-end that serves as the starting point for complementary strand synthesis.

The template polynucleotide of the present invention is capable of forming a loop by the annealing of its 3'-end to itself. This 3'-end annealed to itself is able to serve as a starting point for complementary strand synthesis using itself as template. There are no restrictions on the nucleotide sequence for annealing, provided it allows complementary strand synthesis from its 3'-end. More specifically, for example, 100-200 nucleotides, normally 50-80 nucleotides, and preferably 20-30 nucleotides, from the 3'-end of a polynucleotide, comprise a nucleotide sequence that is complementary to an arbitrary region within the above target nucleotide sequence. At this time, the nucleotides of the annealed 3'-end are preferably completely complementary to the target nucleotide sequence. Although it is not essential for the nucleotides of the 3'-end to be completely complementary, this is an important condition for efficient complementary strand synthesis.

The template polynucleotide of the present invention is capable of forming a loop by the annealing of its 3'-end to itself. Similar to the above loop, this loop is composed of an arbitrary nucleotide sequence, and is present in a state that enables base pairing with another polynucleotide.

In addition, the template polynucleotide of the present invention can have on its 5'-end a nucleotide sequence that is complementary to an arbitrary region in the template itself. When a complementary strand of such a template polynucleotide is synthesized, the 3-end of the synthesized new polynucleotide is able to serve as a starting point of a complementary strand synthesis reaction that uses itself as a template by annealing to its own arbitrary region. The annealing of the 3'-end to itself forms a loop. A primer in the present invention can anneal to a loop formed in this manner.

In this manner, a product of complementary strand synthesis can be reused as a template polynucleotide by making the 5'-end of a template polynucleotide, a nucleotide sequence that is complementary to an arbitrary region in the template. Thus, such a template polynucleotide has a preferable structure for achieving a highly efficient complementary strand synthesis reaction in the present invention.

The template polynucleotide in the present invention can be synthesized enzymatically or chemically. For example, a template polynucleotide can be synthesized by conducting the following steps a) through d). The following steps a) through d) can be said to be a polynucleotide synthesis method for the LAMP method:

a) annealing a first primer to a target nucleotide sequence, and conducting a complementary strand synthesis reaction using this as a starting point, wherein said first primer (i) can provide at the 3'-end a starting point for complementary strand synthesis to a region that defines the 3'-side of one of the strands that compose the target nucleotide sequence, and (ii) has on its 5'-side a nucleotide sequence complementary to an arbitrary region of a complementary strand synthesis reaction product that uses this primer as a starting point;

b) placing, in a condition that allows base pairing, the region to where a second primer is to anneal in the elongation product of the first primer synthesized in step a), wherein said second primer (i) has on its 3'-end a nucleotide sequence providing a starting point for complementary strand synthesis to a region that defines the 3'-side of a target nucleotide sequence in the elongation product that uses the first primer as a starting point, and (ii) has on its 5'-side a nucleotide sequence that is complementary to an arbitrary region of a complementary strand synthesis reaction product that uses this primer as an starting point;

c) annealing said second primer to the region that can form base pairing in step b); and carrying out complementary strand synthesis using this as a starting point; and, d) annealing the 3'-end of the elongation product of the second primer synthesized in step c) to itself, and carrying out complementary strand synthesis using itself as template.

The following provides more specific explanation of the above steps based on FIG. 1. In the following explanation, an example is shown of a process in which a template polynucleotide is produced in the present invention using a first primer (RA) comprising R2 and R1c and a second primer (FA) comprising F2 and F1c. In the following explanation, the first primer and the second primer are tentatively named RA and FA, respectively.

The first primer RA (i) can provide at the 3'-end a starting point for complementary strand synthesis to a region that defines the 3'-side of one of the strands that compose a target nucleotide sequence, and (ii) has on the 5'-side a nucleotide sequence that is complementary to an arbitrary region of a complementary strand synthesis reaction product that uses this primer for an starting point. The region on the 3'-side of RA is referred to as R2, while the region on the 5'-side is referred to as R1c. On the other hand, the second primer FA (i) has in its 3'-end a nucleotide sequence that is capable of providing a starting point for complementary strand synthesis to a region that defines the 3'-side of a target nucleotide sequence in an elongation production that uses the above first primer RA as a starting point, and (ii) on the 5'-side a nucleotide sequence that is complementary to an arbitrary region of a complementary strand synthesis product that uses this primer as an starting point. The 3'-side of FA is referred to as F2, while the 5'-side is referred to as F1c. Moreover, each region that composes the 3'-side and 5'-side of RA and FA respectively comprises a nucleotide sequence complementary to the following regions.

3'-side of RA (R2): R2c
5'-side of RA (R1c): R1
3'-side of FA (F2): F2c
5'-side of FA (F1c): F1

Ultimately, the structure of RA is determined by R2c and R1 of the target nucleotide sequence, while the structure of FA is determined by F2c and F1 in the target nucleotide sequence. Thus, in the present invention, the target nucleotide sequence is required to be a nucleotide sequence in which at least a portion of that nucleotide sequence is either known or is predictable. The portions for which the nucleotide sequence is to be clarified, comprise each of the regions that determine the structures of RA and FA, or regions comprising their complementary nucleotide sequences. R2c and R1c (or F2c and F1c) may be linked to each other or may exist separately. The state of the loop portion formed by self-annealing of the product polynucleotide depends on the relative position of the two regions. The term self-annealing means that a region comprising the 3'-end of a single-stranded polynucleotide hybridizes to the complementary nucleotide sequence of the polynucleotide itself to start complementary strand synthesis using the polynucleotide itself as template. The two regions are preferably not unnecessarily apart to achieve self-annealing of the product polynucleotide more preferentially than annealing of two molecules. Thus, a preferred length of the spacer nucleotide sequence between the two regions is typically 0 to 500 nucleotides. However, in some cases, regions existing too close to each other may be disadvantageous for forming a desirable loop by self-annealing.

More specifically, the loop preferably has a structure that enables the annealing of a new oligonucleotide and a smooth start for the complementary strand synthesis reaction accompanying strand displacement. Thus, more preferably, the primers are designed so that the distance between region R2c and region R1c located on the 5'-side of X2c is 0 to 100 nucleotides, more preferably it is 10 to 70 nucleotides. This value does not include the length of R1c and R2c. The nucleotide length of the loop portion further includes the length corresponding to R2. Also, similar conditions are applied to the distance between region F2c and region F1c in FA.

Regions R2 and R1c (or F2 and F1c) constituting RA and FA are typically arranged continuously without overlapping with respect to the above nucleotide sequence. Alternatively, if R2 (or F2) and R1c (or F1c) share a common nucleotide sequence, they may be placed so that they partly overlap. R2 (or F2) should be placed at the 3'-end at all times since it has to function as a primer. On the other hand, R1c (or F1c) is placed at the 5'-end as described below, to provide a function as a primer to the 3'-end of the complementary strand synthesized using R1c (or F1c) as template. The complementary strand obtained using the oligonucleotide as the synthesis origin serves as the template of the reverse complementary strand synthesis in the next step, and finally, RA and FA are also copied as the template to the complementary strand. The copied 3'-end contains the nucleotide sequence R1 (or F1), and anneals to R1c (or F1c) located within the same strand to form a loop.

To begin with, complementary strand synthesis is carried out by annealing R2 of the first primer to R2c in the target nucleotide sequence (FIG. 1-(1)). When the elongation product of the first primer is converted to a single strand, and complementary strand synthesis is carried out by annealing F2 of the second primer to its F2c, complementary strand synthesis ends when it has reached the 5'-end of the first primer. The elongation product of the second primer synthesized at this time has R1 in its 3'-end. R1 of the 3'-end is a region synthesized using R1c of the 5'-side of the first primer as template. R1 serves as the starting point for complementary strand synthesis by annealing to its own R1c, and complementary strand synthesis is conducted using itself as template (see "recycling products" of FIG. 1-(2)).

The polynucleotide that is produced as a result of the above reaction has a set of complementary nucleotide sequences composed of the target nucleotide sequence and its complementary strand, and a loop that enables base pairing is formed when they hybridize. In addition, F1 comprises in its 3'-end a nucleotide sequence complementary to its own F1c. F1 is a region that is synthesized by using F1c of the second primer as template. Namely, this product is none other than a template polynucleotide in the present invention.

Furthermore, the structures for providing a polynucleotide that can serve as a new starting material for a polynucleotide synthesis reaction is shown as "recycling products" in FIG.

1. The products that are produced by using these structures as templates are all capable of producing new template polynucleotides.

Furthermore, in FIG. 1, a step is shown in which complementary strand synthesis is carried out by a template polynucleotide that has been produced by the further annealing of its 3'-end to itself. As a result, a template polynucleotide having two sets of complementary target nucleotide sequences is produced (FIG. 1-(3)). Furthermore, the sequence which composes a target nucleotide sequence in FIG. 1-(3) is a nucleotide sequence that composes between F2 and R2c and between its complementary nucleotide strands R2 and F2c.

The above reaction actually proceeds in parallel even in the complementary strand of the target nucleotide sequence. Namely, the reaction starts from complementary strand synthesis of the second primer, proceeds through the elongation product of the first primer (FIG. 1-(2')), and produces a template polynucleotide having two sets of complementary target nucleotide sequences (FIG. 1-(3')). The template polynucleotide shown in FIG. 1-(3) and the template polynucleotide shown in FIG. 1-(3') have mutually complementary nucleotide sequences.

Next, in carrying out step b) in a reaction for synthesizing a template polynucleotide based on the LAMP method, namely the step of placing, in a condition that allows base pairing, the region to which the second primer in an elongation product of the first primer synthesized in step a) is to anneal, it is advantageous to use an outer primer. In the present invention, outer primers refer to a primer comprising a nucleotide sequence that is complementary to the upstream from the first primer and second primer that are annealed to the target nucleotide sequence. In the present invention, upstream refers to the 3'-side in the template. Thus, the regions that are annealed by an outer primer are regions on the 5'-sides as viewed from the first primer and second primer.

For example, FIG. 1-(1) describes an outer primer R3 that anneals to R3c located on the 3'-side of region R2c to which RA anneals. Similarly, in its complementary strand, outer primer F3 can anneal to F3c located on the 3'-side of the region to which FA anneals. An oligonucleotide having a nucleotide sequence that functions as a primer at least on its 3'-side can be used for the outer primer. Both the first primer and second primer can be used as two of the three types of primers in the present invention. On the other hand, the outer primer described here does not necessarily compose the three types of primers of the present invention. The outer primer is used to synthesize a template polynucleotide.

In contrast to the first primer and second primer that are normally composed of a combination of two primers, the outer primer may be composed of an arbitrary number of primers. In the present invention, a typical outer primer consists of two outer primers capable of providing a starting point for complementary strand synthesis to the upstream of each of the first primer and second primer. However, the method of the present invention can be practiced even in the case where an outer primer is arranged only to either the first primer or the second primer. Alternatively, a plurality of outer primers may be combined with each or one of the first primer and second primer. In any case, when accompanying complementary strand synthesis from farther upstream, a product of a complementary strand synthesis reaction that uses the first primer and second primer as replication origin can be produced efficiently.

Complementary strand synthesis from an outer primer in the present invention is designed so that it begins later than the complementary strand synthesis using the first and second primers as replication origin. The simplest method for accomplishing this is to make the concentrations of the first and second primers higher than that of the outer primer. More specifically, normally by using primers having a difference in concentrations of 2-50 times, and preferably 4-10 times, complementary strand synthesis from the first and second primers can be preferentially conducted. In addition, the timing of synthesis can also be controlled by setting the melting temperature (Tm) of the outer primer to be lower than Tm of the first and second primers.

Namely, by designing the Tm of the outer primer to (outer primer F3:F3c)$\leq$(F2c/F2) with respect to inner primer FA, nucleic acid amplification can be carried out efficiently. It is preferable to design each region that composes FA so that annealing between (F1c/F1) takes place preferentially to (F2c/F2). In the design, Tm, the constituent nucleotides, and so forth are taken into consideration. Moreover, the high possibility that the annealing between F1c/F1 will proceed preferentially since it is an intramolecular reaction, is also taken into consideration. Similar conditions are also considered in the design of RA that anneals to the FA elongation product.

As a result of creating such a relationship, stochastically ideal reaction conditions can be achieved. Melting temperature (Tm) can theoretically be calculated if other conditions are constant by the length of the complementary strand that is annealed and the combination of nucleotides that compose base pairs. Thus, a person with ordinary skill in the art is able to easily arrive at the preferable conditions based on the teachings of the present description.

Moreover, in order to adjust the timing of annealing of outer primer, a phenomenon referred to as "contiguous stacking" can be applied. Contiguous stacking is a phenomenon in which an oligonucleotide that is unable to anneal alone can be made to anneal by placing it adjacent to a double-stranded portion (Chiara Borghesi-Nicoletti et al., Bio Techniques 12, 474-477, 1992). In other words, the outer primer is made placed adjacent to a first primer and second primer, and designed so that the outer primer is unable to anneal alone under the incubation conditions. When this is done, since it is possible for the outer primer to anneal only after the first and second primers have annealed, annealing of the first and second primers inevitably precedes. Based on this principle, an example of setting the nucleotide sequence of an oligonucleotide required as a primer for the series of reactions is described in the Examples.

In the above reaction, a polynucleotide sample that contains a target nucleotide sequence can use an arbitrary polynucleotide that is capable of serving as a template of complementary strand synthesis. Specific examples can include DNA, RNA, as well as their derivatives and chimeric molecules. Moreover, in addition to natural polynucleotides such as genome DNA and mRNA, polynucleotides artificially integrated into plasmids, phages, or such may also be used for the polynucleotide sample. The polynucleotide sample may be used in not only the purified state, but also the crude state. Polynucleotides present within cells are also applicable to in situ synthesis.

Next, in the present invention, at least three types of primers are used that are capable of providing a starting point for complementary strand synthesis to different regions of a loop. The loops to which the primers impart the starting points of complementary strand synthesis includes not only the loops present in the above template polynucleotides, but also loops formed by new polynucleotides produced as a result of complementary strand synthesis using their 3'-ends or any of the primers as a starting point.

A template polynucleotide has at least the following two loops:

1. a loop formed by the hybridization of a target nucleotide sequence; and,
2. a loop formed by the annealing of the 3'-end of a template polynucleotide to itself.

In the case where the template polynucleotide has two or more sets of complementary nucleotide sequences, and the complementary nucleotide sequences are alternately arranged, loops are formed on the template polynucleotide corresponding to the number of complementary nucleotide sequences. For example, a polynucleotide is assumed that is composed of a certain nucleotide sequence A and its complementary nucleotide sequence a. An example of the state in which a plurality of sets of complementary nucleotide sequences is alternately arranged, can be represented as shown below.

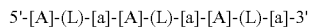

5'-[A]-(L)-[a]-[A]-(L)-[a]-[A]-(L)-[a]-3'

In this example, three loops can be formed when hybridization occurs between adjacent [A] and [a]. The portions where loops are formed due to hybridization of complementary nucleotide sequences are indicated with -(L)-. Moreover, there is an additional loop formed by annealing of the 3'-end to itself, resulting in a total of four loops being formed by this template polynucleotide. When the 3'-end forms a loop by annealing to itself, a portion of the nucleotide sequence of [a] is used for annealing. Thus, [a] of the 3'-end has a region that is a nucleotide sequence complementary to [A] while being used for annealing to itself.

Furthermore, there are no restrictions on the number of complementary nucleotide sequences that can be present in a template polynucleotide of the present invention. Thus, a template polynucleotide composed of [A] and [a] can be represented by a formula like that shown below. In this formula, n refers to any natural number.

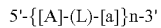

5'-{[A]-(L)-[a]}n-3'

On the other hand, a loop formed by a new polynucleotide produced as a result of complementary strand synthesis that uses the 3'-end of a template polynucleotide or any of the primers as a starting point is specifically formed in the following manner. To begin with, a complementary strand synthesis reaction can be carried out for the template polynucleotide by annealing its 3'-end to itself and using itself as template. This reaction proceeds continuously if allowed to be in a state in which base pairing can be repeated between the 3'-end and the region to which it anneals. As a result, the nucleotide sequence complementary to the template polynucleotide is repeatedly elongated. Thus, in the case where the template polynucleotide is composed of one set of complementary nucleotide sequences, the number of complementary nucleotide sequences in the new polynucleotide obtained by complementary strand synthesis doubles with each repetition of the complementary strand synthesis reaction. Here, when two sets of complementary nucleotide sequences are respectively hybridized in the newly produced polynucleotide, a number of loops occur that corresponds to the number of sets of complementary nucleotide sequences (refer to, for example, FIG. 1-(4) or FIG. 1-(5)). Among these loops, some of the loops are those originally present in the template polynucleotide. Other loops are composed of loop complementary nucleotide sequences of the template polynucleotide. New loops produced in this manner are also included in the loops to which a primer anneals in the present invention.

Moreover, a loop formed by a new polynucleotide produced by the annealing of a primer to a loop present in a template polynucleotide and by using this as a starting point for complementary strand synthesis, is also included in the loops of the present invention. For example, a complementary strand can be synthesized by using as a starting point a primer capable of providing a starting point for complementary strand synthesis to a loop formed by annealing of the 3'-end of a template polynucleotide to itself. This product becomes a polynucleotide comprising a nucleotide sequence complementary to the template. Similar to template polynucleotide, this polynucleotide forms a loop by hybridization with a complementary nucleotide sequence. Namely, a polynucleotide is produced that has a loop comprising a nucleotide sequence that is complementary to a loop present in the template polynucleotide.

A primer capable of providing a starting point for complementary strand synthesis to a new loop formed in this manner is included in the primers of the present invention. Alternatively, as was previously described, in the case where a template polynucleotide contains a nucleotide sequence complementary to an arbitrary region on its own 5'-end, the 3'-end of polynucleotide synthesized by using this as a template is capable of forming a loop by annealing to itself. In the present invention, a primer can also be used that is capable of providing a starting point for complementary strand synthesis to a loop formed in this manner.

Furthermore, when the 5'-end of a template polynucleotide contains a nucleotide sequence complementary to an arbitrary region of itself, the 5'-end is able to form a loop by hybridizing to itself. A loop of the 5'-end is also in a state that allows base pairing. However, normally, only a small region extending from the loop to the 5'-end is eligible for complementary strand synthesis from a primer that provides a starting point for complementary strand synthesis to this loop.

In the present invention, three or more types of primers of the present invention are used that are capable of serving as a starting point for complementary strand synthesis in at least one type, preferably two types, or three or more types of loops selected from several types of loops as previously mentioned. "Three or more types" refers to three primers or more providing a starting point for complementary strand synthesis at mutually different locations.

At least three types, preferably four types, or five or more types of primers can be combined in the present invention. It should be noted that "mutually different locations" refer to the location of the 3'-end of each primer being mutually different when the primer has been annealed. Thus, those nucleotide sequences required for annealing may be partially overlapping. However, in the case where the regions required for annealing overlap, since competition occurs between primers, it is preferable to design the nucleotide sequences of the primers so that they can be annealed to mutually independent regions as much as possible. Moreover, complementary strand synthesis can be expected to proceed more rapidly by designing the nucleotide sequences of the primers so that there is minimal overlapping even with respect to those regions subject to hybridization and annealing in the template polynucleotide. Thus, for example, the combination of a template polynucleotide and three or more types of primers that anneal to mutually different loops formed in a complementary strand synthesis product that is produced by using the template polynucleotide as template can be said to be a preferable primer combination for the present invention.

A nucleotide sequence that composes a primer of the present invention contains a nucleotide sequence that is complementary to the nucleotide sequences of the above-mentioned plurality of loops. Its 3'-side is required to impart a starting point for complementary strand synthesis to those loops. Thus, at least its 3'-end should be located within the loops. However, all of the nucleotide sequences required for annealing need not be arranged within the loops. Thus, as long as the primer is able to impart a starting point for complementary strand synthesis under the required reaction conditions, a portion of the nucleotide sequences required for annealing may overlap with the nucleotide sequence that composes the double-strand polynucleotide adjacent to the loop. In addition, an arbitrary nucleotide sequence may be also added to the 5'-side of the primer. In the present invention, the previously mentioned LAMP primer can be used as a primer that provides a starting point for complementary strand synthesis to a loop present in a template polynucleotide.

The LAMP method (Nucleic Acid Res. 2000, Vol. 28, No. 12 e63, WO 00/28082) is a method that allows highly isothermal complementary strand synthesis reactions by combining a primer that serves as a starting point for complementary strand synthesis by annealing a template polynucleotide to its own 3'-end, while also being able to impart a starting point for complementary strand synthesis to a loop formed at this time. At least two primers are used in the LAMP method.

[1] First primer: The first primer can provide (i) at its 3'-end a starting point for complementary strand synthesis to a region that defines the 3'-side of one of the strands that compose a target nucleotide sequence, and (ii) on the 5'-side a nucleotide sequence that is complementary to an arbitrary region of a complementary strand synthesis reaction product that uses this primer as an starting point,

[2] Second primer: The second primer has on its 3'-end a nucleotide sequence capable of providing a starting point for complementary strand synthesis to a region that defines the 3'-side of a target nucleotide sequence in an elongation product that uses the above first primer as a starting point, and (ii) on the 5'-side a nucleotide sequence that is complementary to an arbitrary region of a complementary strand synthesis reaction product that uses this primer as an starting point, that is, the first primer and second primer used for synthesis of the above template polynucleotide are able to compose a portion of at least the three types of primers in the polynucleotide synthesis method based on the present invention. In other words, the present invention can be carried out by combining a third primer that is capable of providing a starting point for complementary strand synthesis at a location that differs from the above first and second primers within a template polynucleotide or loop formed by a reaction product. In the present invention, in addition to the primers required for synthesis of a target nucleotide sequence, the primer that is additionally combined is referred to, sometimes, as a loop primer.

It is not essential that the primer used for template polynucleotide synthesis is also used as a primer for synthesis of a target nucleotide sequence. A primer for synthesizing a target nucleotide sequence may be added separate to the primer for synthesizing a template polynucleotide. However, it is usually more practical to compose a reaction with as few elements as possible.

A particularly preferable loop primer in the present invention is that which is capable of providing an starting point for complementary strand synthesis to a region between R1 and R2 (or between F1 and F2). When either a loop primer capable of annealing between R1 and R2 or between F1 and F2 is combined with a LAMP primer, three types of primers are used. Moreover; if primers capable of annealing between both R1 and R2 and between F1 and F2 are combined together, in addition to the two types of loop primers for the LAMP primers, a total of four types of primers are used. In the present invention, a loop primer can be expected to have the action of accelerating the polynucleotide synthesis reaction by combining at least one type, and preferably two or more types.

This loop primer anneals to a loop containing R2 (refer to, for example, FIG. 1-(4)). This loop is composed of a region extending from R1 to R2 in the target nucleotide sequence (however, in FIG. 1-(4), R2 is contained, but not R1). For such a loop, the loop primer of the present invention can be a nucleotide having an arbitrary nucleotide sequence comprising a nucleotide sequence complementary to the nucleotide sequence that composes the loop.

However, as is clearly shown in the examples, a polynucleotide can be synthesized more efficiently by selecting a region within a loop. For example, a loop primer capable of providing a replication origin to a region that does not overlap with R1c, namely one closer to the 3'-side than R1c, enhances the reaction efficiency of the LAMP method considerably.

Ultimately, examples of preferable loop primers that are combined when applying the present invention to the LAMP method, include those primers that satisfy the following condition: namely, those that provide a starting point for complementary strand synthesis to a loop (i) formed by a template polynucleotide and/or polynucleotide produced by a reaction of template polynucleotide with a first primer and a second primer, and (ii) to which the first primer and the second primer cannot anneal. The loop primer should be able to anneal to a region in which a 3'-end is arranged, which serves as the starting point for complementary strand synthesis within the loop. Thus, not only in the case in which the nucleotide sequence required for annealing is contained completely within the loop, but also in the case in which a portion of that sequence overlaps with a region other than the loop, the preferable condition can be said to be satisfied if the 3'-end is located within the loop. For example, the Examples show that even when a portion of the nucleotide sequence to which the loop primer is to anneal extends to a double-stranded structure adjacent to the loop, reaction accelerating effects that are similar to those seen when the region to be annealed is arranged completely within the loop can be obtained.

The preferable positional relationship between loop primer and nucleotide sequence that composes a template polynucleotide is shown in FIG. 3. FIG. 3 depicts complementary strand synthesis using the 3'-end of F1 that anneals to itself as a starting point. FIG. 3 indicates the same structure as FIG. 1-(2'). Namely, once the complementary strand synthesis shown in this figure is over, a template polynucleotide of the present invention is completed. As shown in FIG. 3, loop primer R is a primer that anneals to a loop containing R2. It should be noted that FIG. 3 is provided to indicate a region to which loop primer R anneals. The complementary strand synthesis from loop primer R annealed to the structure of FIG. 3 actually ends as soon as the 5'-end is reached. When complementary strand synthesis is carried out by annealing to the loop of a similar nucleotide sequence formed in the reaction product produced from template polynucleotide, the complementary strand synthesis that uses loop primer R as a starting point, contributes to the improvement of reaction efficiency.

When the present invention is applied to the LAMP method, it is preferable that the loop primers are able to anneal under the same conditions as the conditions of the LAMP method. The fact that all reactions can be carried out without changing the temperature is a major advantage of the LAMP method. When combining loop primers for the present invention as well, it is ideal to use loop primers under the same temperature conditions as the LAMP method so as not to lose this advantage. In order to accomplish this, the Tm of the loop primers is designed to be at the same level as the primers for the LAMP method. Tm is determined by the types and number of nucleotides that compose the primers as well as the salts and various types of components that have an effect on Tm contained in the reaction solution. Thus, in the present invention, Tm of the loop primers is adjusted by the nucleotide sequences of the primers to match the conditions of the reaction solution for the LAMP method. One skilled in the art is able to impart a suitable Tm by adjusting the nucleotide sequences of the primers to match the various conditions. These conditions relating to the loop primers are also applied to the loop composed by F1c and F2c (or by R1c and R2c).

The structure shown in FIG. 1-(4) is the product produced as a result of repeating a complementary strand synthesis reaction in which the template polynucleotide uses itself as a template. That loop is composed of a nucleotide sequence that is complementary to the loop of the template polynucleotide. Primers that anneal to the template polynucleotide are unable to anneal as primers to a nucleotide sequence complementary to the template polynucleotide. In other words, a preferable loop primer in the present invention is able to impart a starting point for complementary strand synthesis to a loop formed on a new polynucleotide that was produced by a synthesis using a template polynucleotide as template. As a result of employing this relationship, complementary strand synthesis that uses a template polynucleotide as template and complementary strand synthesis that uses a newly produced polynucleotide as template proceed. As a result, more polynucleotides are rapidly produced in a short period of time.

As already described above, the 3'-side of a loop primer of the present invention serves as a starting point for complementary strand synthesis by annealing to the loop. In contrast, it is possible to arrange on the 5'-side of a loop primer, a nucleotide sequence that is complementary to a nucleotide sequence that composes an arbitrary region of a complementary strand synthesized by using the 3'-end of the loop primer as a starting point. In the present invention, a preferable example of a nucleotide sequence for the nucleotide sequence arranged on the 5'-side of a loop primer, is a nucleotide sequence substantially identical to the nucleotide sequence arranged on the 5'-side of the previously mentioned inner primer (F1c or R1c). Herein, substantially identical sequences include cases in which the 3'-end of a complementary strand produced by using a nucleotide sequence arranged on the 5'-side of a loop primer as template is able to provide a starting point for complementary strand synthesis to a region to which is annealed the 3'-end of a complementary strand produced by using the nucleotide sequence arranged on the 5'-side of the above inner primer RA or FA as template.

For example, a nucleotide sequence substantially identical to the nucleotide sequence R1c arranged on the 5'-side of RA can be arranged in loop primer R that anneals to a loop containing the nucleotide sequence of primer RA. Similarly, a nucleotide sequence substantially identical to the nucleotide sequence that composes F1c can be arranged on the 5'-side in loop primer F that anneals to a loop that contains the nucleotide sequence of inner primer FA.

An elongation product produced by a loop primer having a nucleotide sequence complementary to itself on the 5'-side is able to impart a nucleotide sequence complementary to itself on the 3'-end of a complementary strand produced by using this as template. As a result, products of loop primers also have structures that function as LAMP recycling products. Thus, the LAMP nucleic acid amplification reaction is also triggered by a loop primer, making it possible to anticipate a high amplification rate.

As is clear from the above explanation, when applying the LAMP method to the polynucleotide synthesis method of the present invention, if an above-mentioned first primer, second primer, and loop primer are used, a template polynucleotide can be obtained based on a target nucleotide sequence, and moreover, the polynucleotide synthesis method according to the present invention can be carried out. In other words, if the following components are incubated together with a target nucleotide sequence, the polynucleotide synthesis method of the present invention can be carried out. These reaction components may be mixed in any order or mixed simultaneously. By further adding an outer primer (to be described later) to this reaction system, all steps can be carried out at the same temperature, targeting a double-stranded polynucleotide sample.

- a polynucleotide sample containing a target nucleotide sequence
- a first primer
- a second primer
- a loop primer (one type, or two or more types)
- a DNA polymerase capable of catalyzing complementary strand synthesis accompanying strand displacement
- a substrate for complementary strand synthesis Moreover, if these components are incubated under conditions that allow complementary strand synthesis, the polynucleotide ultimately synthesized based on the target nucleotide sequence will continue to produce a new template polynucleotide. All the newly produced polynucleotides are used as materials for synthesizing new polynucleotides. Namely, polynucleotide amplification occurs. The present invention includes polynucleotide amplification methods achieved in this manner. Amplification efficiency can be improved considerably by amplifying polynucleotides based on the polynucleotide synthesis method of the present invention. For example, by carrying out an amplification method based on the present invention combining a loop primer with a LAMP primer under preferable conditions, the reaction time can be shortened to half or less compared to when a loop primer is not present.

The following provides an explanation of a reaction in which a double-stranded polynucleotide is amplified by using RA (first primer), FA (second primer), loop primer F, and loop primer R and combining with a DNA polymerase that catalyzes a strand displacement type of complementary strand synthesis reaction, also referring to the basic principle illustrated in FIGS. 1 and 2. In this example, RA and FA compose a set consisting of a first primer and second primer for synthesizing a target nucleotide sequence. Loop primer F is capable of providing a starting point for complementary strand synthesis to a loop containing F2, while loop primer R is capable of providing a starting point for complementary strand synthesis to a loop containing R2.

As already described, a template polynucleotide of the present invention is obtained when the step of conducting complementary strand synthesis by annealing the 3'-end shown in FIG. 1-(2) or FIG. 1-(2') to itself is completed. Moreover, in the loop of this template polynucleotide, complementary strand synthesis is carried out by annealing by RA (FIG. 1-(2)) or FA (FIG. 1-(2')), respectively, and the 3'-end of template polynucleotide once again becomes a single strand due to displacement. After becoming a single strand, the 3'-end anneals to itself and complementary strand synthesis proceeds. As a result, the products shown in FIG. 1-(3) and FIG. 1-(3') are produced. In this manner, the cycle of complementary strand synthesis consisting of annealing of primer RA or primer FA to a loop, complementary strand synthesis, displacement of the 3'-end of the template polynucleotide, and finally, annealing of the 3'-end to itself, is repeated.

At this time, as a result of the elongation of the 3'-end of the template polynucleotide, which uses itself as template, the product of complementary strand synthesis that uses RA or FA annealed to the loop as a replication origin is displaced, resulting in the production of a new single-stranded polynucleotide. This single-stranded polynucleotide has nucleotide sequences complementary to itself on its 3'-end and 5'-end. In other words, products that have a structure identical to FIG. 1-(2) and FIG. 1-(2') are made. These become new template polynucleotides and a similar reaction proceeds repeatedly. The entire reaction mechanism up to this point has been clarified as the LAMP method.

In FIG. 1-(3), primer FA annealed to the loop elongates while displacing the double-stranded structure of the template polynucleotide until it finally reaches the 5'-end. At this time, the 3'-end side of the displaced template polynucleotide has a single-stranded structure. Consequently, nucleotide sequences that are complementary to themselves are mutually hybridized. The product formed in this manner has the structure shown in FIG. 1-(4). Namely, a loop is formed by annealing the 3'-end of the template polynucleotide to itself simultaneous to hybridization of complementary nucleotide sequences. The loop formed due to hybridization of complementary nucleotide sequences is a complementary strand that is a copy of the loop portion of the template polynucleotide used as the original. As is clear from the drawings, this loop contains R2, and FA and RA are unable to anneal to it. However, loop primer R is able to anneal to the loop containing R2. Therefore, complementary strand synthesis begins by annealing loop primer R to the loop that contains R2.

On the other hand, a polynucleotide amplification reaction based on the known LAMP method continues. Namely, the amplification reaction due to the elongation reaction by the template polynucleotide that uses itself as template and by primer FA that anneals to the loop, continues. This reaction itself is none other than a polynucleotide amplification reaction in which new template polynucleotides are continuously produced. It should be noted that the amplification reaction starting in FIG. 1-(4) that has previously been clarified with the LAMP method is not shown herein.

Accompanying elongation of loop primer R, both template polynucleotide and the elongation product of primer FA are displaced to enable base pairing, again resulting in the production of a template polynucleotide. The elongation product of loop primer R in particular shown in FIG. 1-(6) has a structure that allows annealing of three types of primers consisting of loop primer F, loop primer R, and FA. This type of product cannot be produced with the known LAMP method. The method of the present invention produces the template polynucleotide shown in FIG. 1-(6) separate to the known product based on the LAMP method. The template polynucleotide shown in FIG. 1-(6) starts an additional polynucleotide amplification reaction together with a loop primer. In this manner, the reaction in which a new polynucleotide is further produced, proceeds separately from the complementary strand synthesis known in the LAMP method. As a result, the synthesis efficiency of complementary strand synthesis is dramatically improved, and the reaction time can be considerably shortened.

Furthermore, in the structure shown in FIG. 1-(6), primer RA is able to anneal to the region containing R2c near the 5'-end. However, since a primer that anneals to this location is only eligible for complementary strand synthesis with respect to the small region to the 5'-end, it is not shown in FIG. 1-(6).

The following description continues to provide an explanation of the type of products that are produced when the reaction of the present invention is allowed to continue further. The elongation product produced from loop primer R in FIG. 1-(4) has the structure shown in FIG. 1-(6). In FIG. 1-(6), a structure is shown in which two loop primers and one primer FA anneal in the same manner as FIG. 1-(5). Among these, the elongation products of the two loop primers are completely displaced to produce a single-stranded polynucleotide by a complementary strand synthesis reaction from the 3'-end in which the polynucleotide shown in FIG. 1-(6) itself is used as a template.

On the other hand, complementary strand synthesis in which the polynucleotide shown in FIG. 1-(6) uses itself as template is completed. Complementary strand synthesis starts in the loop including F2c comprising FIG. 2-(7) by annealing primer FA to that loop. Since the loop containing F2c comprising FIG. 2-(7) is actually already formed in FIG. 1-(6), a reaction in which FA anneals to this loop proceeds in parallel with the reaction that produces FIG. 2-(7). In any case, the region extending from the polynucleotide loop shown in FIG. 2-(7) to the 3'-end is displaced resulting in a single strand due to elongation of the FA annealed to the loop.

The complementary nucleotide sequences contained in the region that has become a single strand are respectively hybridized, resulting in the structure shown in FIG. 2-(8). Furthermore, there is a high possibility that hybridization with complementary nucleotide sequences in physically close regions will preferentially occur in the polynucleotide that has become a single strand. Thus, hybridization with an adjacent region takes precedence over hybridization with other molecules such as various primers or complementary nucleotide sequences located farther away. As is clear from the drawings, loop primer R anneals to the 3'-end of the polynucleotide shown in FIG. 2(8). In addition, two loops are formed to which primers FA and RA are able to anneal. In addition to the elongation of each primer that has annealed to the loop, they are also displaced by an elongation reaction from loop primer R resulting in a single-stranded polynucleotide, which dissociate from the polynucleotide of FIG. 2-(8).

The double-stranded polynucleotide formed as a result of complementary strand synthesis by loop primer R does not form any new loops, and becomes the stable double-stranded polynucleotide of FIG. 2-(12). Although this polynucleotide is stable and is a double-stranded polynucleotide under the reaction conditions of the LAMP method, it can be used as a new template. In other words, even though it is a double-stranded polynucleotide unaccompanied by a loop as shown in FIG. 2-(12), it is capable of starting a new reaction by serving as a template for FA and RA. The structure shown in FIG. 2-(12) does not have regions R3 or F3 (FIG. 1-(1)) to which an outer primer is to anneal, which was used when the double-stranded polynucleotide was used as a template polynucleotide. However, in the structure shown in FIG. 2-(12), since a plurality of regions to which primers FA and RA are able to anneal are arranged consecutively, the upstream FA can be expected to demonstrate the function of an outer primer for downstream FA. The reaction in which double-stranded polynucleotide is used as a template is described later.

The single-stranded polynucleotide produced by using the polynucleotide of FIG. 2-(8) as template has the three types of structures shown in FIG. 2-(9), FIG. 2-(10), and FIG. 2-(11). The relationships between the templates and primers that yield each structure are indicated below. Each polynucleotide is indicated by the number in parenthesis ( ) in FIG. 2.

| Template | (7) | (8) | (8) |
|---|---|---|---|
| Primer | FA | RA | FA |
| Single strand polynucleotide | (9) | (10) | (11) |

The following reaction proceeds from these single-stranded polynucleotides as a result of the annealing of primers corresponding to the loop formed by each polynucleotide to the polynucleotide. To begin with, polynucleotide of FIG. 2-(9) yields the products shown in FIG. 2-(14) and FIG. 2-(15) as elongation products by primer FA annealing to F2c and primer RA annealing to R2c. These products both dissociate as single-stranded polynucleotides as a result of being displaced due to the complementary strand synthesis reaction from loop primer R annealed to a loop containing R2 of polynucleotide FIG. 2-(9) The two polynucleotides shown in FIG. 2-(14) and FIG. 2-(15) have a structure equivalent to the series of polynucleotides of FIG. 1-(2) and FIG. 1-(3) indicated as "recycling products" in FIG. 1. A strict comparison reveals that the arrangement of R2 and F2 (or R2c and F2c) within the loop when the loop is formed, differs between the two. However, these polynucleotides both lead to the production of template polynucleotides and compose a polynucleotide amplification reaction.

Next, attention is focused on polynucleotide of FIG. 2-(10). Elongation products of primer FA and primer RA are also produced from these polynucleotides as single-stranded polynucleotides of FIG. 2-(15') and FIG. 2-(16) in nearly the same manner as FIG. 2-(9). These polynucleotides are displaced accompanying complementary strand synthesis of loop primer R, and dissociate as single-stranded polynucleotides. The polynucleotide shown in FIG. 2-(15') has a structure equivalent to FIG. 1-(3'). FIG. 2-(16) is also a template polynucleotide having a 3'-end capable of annealing to itself in the same manner as FIG. 1-(3). Thus, both function as template polynucleotides or as templates for new complementary strand reactions.

Moreover, polynucleotide of FIG. 2-(11) also produces a starting material for a new reaction in the same manner as the above polynucleotide. Namely, FIG. 2-(17) and FIG. 2-(18) are respectively produced as elongation products of primer FA and primer RA that anneal to the loop. These products are displaced accompanying complementary strand synthesis of loop primer R, and dissociate as single-stranded polynucleotides. The produced FIG. 2-(18) is none other than a template polynucleotide having a 3'-end capable of annealing to itself in the same manner as FIG. 1-(3), while FIG. 2-(17) is none other than template polynucleotide provided with a 3'-end capable of annealing to itself in the same manner as FIG. 1-(3').

FIG. 2-(13) derived from loop primer F is thought to undergo reactions such as complementary strand synthesis followed by annealing of primer FA, complementary strand synthesis from loop primer R that anneals to the region displaced by the above complementary strand synthesis, and the production of single-stranded polynucleotide by dissociation of the elongation product from the above primer FA. These reactions are not shown since they are not thought to lead to the production of new template polynucleotides.

Ultimately, all of the products shown in FIG. 2-(14) through FIG. 2-(18) function as starting substances for new complementary strand synthesis by becoming template polynucleotides in the present invention. Namely, they lead to the formation of structures shown as "recycling products" in FIG. 1. The polynucleotide amplification method based on the present invention continues in this manner.

A template polynucleotide of the present invention can be synthesized by using as a starting material, a target nucleotide sequence comprised in a polynucleotide double-stranded state. A method for carrying out complementary strand synthesis by annealing a primer to a target nucleotide sequence in a double-stranded state has been reported by the inventors (23rd Annual Meeting of the Japan Molecular Biology Society, Dec. 13-16, 2000, Kobe, Nagamine, K., Watanabe, K., Ohtsuka, K., Hase, T., and Notomi, T. (2001), Loop-mediated isothermal amplification reaction using a non-denatured template, Clin. Chem. 47, 1742-1743).

In FIG. 1, a template polynucleotide is synthesized by using a single-stranded target nucleotide sequence as a starting substance. However, if a method is applied in which a target nucleotide sequence contained in a polynucleotide in a double-stranded state is used as the starting substance, the step of denaturing to a single strand can be omitted, and the double-stranded polynucleotide can be used directly as a starting substance. A double-stranded polynucleotide of the present invention includes, for example, cDNA and genome DNA. In addition, various vectors into which these DNAs have been inserted can be also used as double-stranded polynucleotides of the present invention. On the other hand, single-stranded polynucleotides include those obtained by denaturing double-stranded polynucleotides with heat, alkaline, or such, and those that originally exist as single-stranded polynucleotides such as mRNAs. The double-stranded polynucleotides of the present invention may be purified or crude nucleic acids. Moreover, the method of the present invention is also applicable to nucleic acid in cells (in situ). In-situ genomic analysis can be achieved using a polynucleotide in cells as template.

When a cDNA is used as a template in the present invention, the step of cDNA synthesis and the method of polynucleotide synthesis according to the present invention can be carried out under the same conditions. When first strand synthesis of cDNA is carried out using RNA as template, a double-stranded polynucleotide of a DNA-RNA hybrid is formed. The method for synthesizing a polynucleotide can be conducted using the double-stranded polynucleotide as template of the present invention. When a DNA polymerase used in a method for synthesizing a polynucleotide of the present invention has a reverse transcriptase activity, the polynucleotide synthesis can be achieved using a single enzyme under the same conditions. For example, Bca DNA polymerase is a DNA polymerase having strand-displacing activity as well as reverse transcriptase activity. A method for synthesizing a polynucleotide according to the present invention can be also used after the formation of complete double-stranded cDNA by the second strand synthesis.

When a template polynucleotide is synthesized from a target nucleotide sequence in a double-stranded polynucleotide, an arbitrary primer is first mixed with the double-stranded polynucleotide, and the mixture is incubated under conditions ensuring complementary strand synthesis using the primer as the starting point. Herein, the arbitrary primer is used to place in condition for base pairing, the region to which the first primer will anneal to. Thus, the arbitrary primer is required to have the ability to anneal to the complementary strand of the polynucleotide strand in the target nucleotide sequence, to which the first primer anneals. Further, the strand extension in the complementary strand synthesis using the arbitrary primer of the present invention as the replication origin should proceed toward the region to which the first primer anneals. In other words, the primer can anneal to an arbitrary portion of the region, which region serves as the template in a complementary strand synthesis using the first primer as a starting point. The arbitrary primer can be selected from arbitrary regions so long as it meets the criteria. For example, the second primer can be also used as the arbitrary primer. The use of the outer primer is one of the preferred embodiments of the present invention, due to the reduced number of necessary reaction components.

Thus, in the step a) of the reaction for synthesizing a template polynucleotide based on LAMP method, i.e. the step in which the first primer anneals to the target nucleotide sequence to start the complementary strand synthesis, base pairing with the first primer can be ensured by displacing one of the two strands of the double-stranded polynucleotide in complementary strand synthesis using the arbitrary primer as a starting point. By choosing such a condition, the method for synthesizing can be conducted without changing temperature. A condition which ensures the annealing of the arbitrary primer and double-stranded polynucleotide, and complementary strand synthesis using this primer as a starting point, is practically a condition where the following multiple steps can be achieved without changing the reaction condition:

i) annealing of the primer to a double-stranded polynucleotide template; and ii) proceeding with complementary strand synthesis using the annealing primer as the replication origin.

It was believed that a primer could anneal to a nucleic acid strand only if the region to which the primer anneals is single-stranded. Thus, when a double-stranded polynucleotide is used as a template, the nucleic acid had to be subjected to a step that converts the nucleic acid into single strands by denaturation prior to the primer annealing. However, the reaction of complementary strand synthesis using a primer as a starting point can be achieved by incubating the template with the primer under conditions where the double strand is destabilized by whatever means without completely converting the double stand into single strands. The condition under which the double-stranded nucleic acid is heated up to nearly the melting temperature (hereinafter abbreviated as Tm) can be exemplified as such a double strand-destabilizing condition. Alternatively, the addition of a Tm regulator is also effective.

In a method for synthesizing a polynucleotide of the present invention, a reaction comprising a series of steps is carried out in the presence of a buffer giving a pH suitable for the enzyme reaction, salts required for primer annealing and maintaining the catalytic activity of the enzyme, preservatives for the enzyme, and in addition if needed, a melting temperature (Tm) regulator, and such. The buffer with a buffering action in a range from neutral to weak alkaline pH, such as Tris-HCl, is used in the present invention. The pH is adjusted depending on the type of DNA polymerase used. Examples of salts to be added to maintain the enzyme activity and to modify the melting temperature (Tm) of the polynucleotide include KCl, NaCl, $MgCl_2$, $MgSO_4$, $(NH_4)_2SO_4$, etc. Enzyme preservatives include bovine serum albumin and sugars.

Further, typical melting temperature (Tm) regulators include betaine, proline, dimethylsulfoxide (hereinafter abbreviated as DMSO), formamide, and trimethylamine N-oxide (hereinafter, abbreviated as TMANO). When a melting temperature (Tm) regulator is used, annealing of the above-mentioned oligonucleotide can be regulated within a limited temperature range. Moreover, betaine (N,N,N-trimethylglycine) and tetraalkylammonium salts effectively contribute to the improvement of the efficiency of strand displacement due to its isostabilizing action. The addition of betaine at a concentration of about 0.2 to 3.0 M, preferably about 0.5 to 1.5 M to the reaction solution is expected to enhance the amplification of polynucleotides of the present invention. Since these melting temperature regulators decrease the melting temperature, a condition giving desired stringency and reactivity is chosen by considering reaction conditions such as salt concentration and reaction temperature.

Suitable temperature conditions for enzyme reactions can be readily chosen by utilizing a Tm regulator. Tm alters depending on the relation of the primer and target nucleotide sequence. Thus, it is preferable to adjust the amount of a Tm regulator so that the conditions that maintain enzyme activity are consistent with the incubation conditions that meet the criteria of the present invention. Based on the disclosure of the present invention, those skilled in the art can readily choose proper amounts of a Tm regulator to be added, depending on the primer nucleotide sequence. For example, Tm can be determined based on the length of the annealing nucleotide sequence and the GC content, salt concentration, and concentration of the Tm regulator.

Annealing of a primer to a double-stranded polynucleotide under such conditions is presumed to be unstable. However, complementary strand synthesis proceeds using the unstable annealed primer as the replication origin when DNAs are incubated with a polymerase-displacing strand. Once a complementary strand is synthesized, primer annealing becomes more stable over time. The DNA polymerases listed below catalyze complementary strand synthesis under conditions ensuring primer annealing to the double-stranded nucleic acid.

All primers used in the present invention can be chemically synthesized. The method for synthesizing a DNA is well known. Alternatively, naturally-occurring polynucleotides can be truncated and altered or linked so as to comprise necessary sequences. Furthermore, all primers used in the present invention can be those that are artificially mutagenized as well as those having a structure of a naturally-occurring DNA. A primer has to meet two requirements: (1) has to be able to form complementary base pairing with a target nucleotide sequence, and (2) provide an —OH group at the 3'-end of the base pair that serves as the complementary strand synthesis origin. Moreover, it is preferable that the primer can be a template for complementary strand synthesis. The backbone of the primer is not restricted to those composed of phosphodiester bonds. For example, the primer may be a phosphothioate or may comprise peptide nucleic acids based on peptide bindings. Further, the nucleotide may be any nucleotide, so long as it forms a complementary base pair. In general, there are five types of naturally occurring nucleotides, namely A, C, T, G, and U; however, analogues such as bromodeoxyuridine, for example, are also included. An oligonucleotide used in the present invention serves not only as a starting point for synthesis, but preferably acts also as a template for complementary strand synthesis.

The primer used in the present invention consists of nucleotides with appropriate lengths to enable base pairing with the complementary strand by maintaining required specificity under a given condition in various types of polynucleotide synthesis reactions in the present invention. Specifically, a primer comprises 5 to 200 nucleotides, and more preferably 10 to 50 nucleotides. The minimal length of a primer recognized by known polymerases catalyzing sequence-dependent polynucleotide synthesis is around 5 nucleotides. Thus, the length of an annealing portion should be longer than 5 nucleotides. In addition, to ensure nucleotide-sequence specificity, a primer comprises stochastically 10 nucleotides or more. On the other hand, an overly long nucleotide sequence is difficult to chemically synthesize. Thus, the above-mentioned length of primers are exemplified as the preferred range. The exemplified length of primers correspond only to the portion annealing to the complementary strand. For example, RA consists of at least two regions, R2 and R1c. Thus, the above exemplified length of primers should be understood as a length corresponding to the length of each region constituting the primer.

The term "template" as used in the present invention refers to a polynucleotide that serves as a template in complementary strand synthesis. Although a complementary strand having a nucleotide sequence that is complementary to a template is a strand corresponding to the template, the relationship between the two is merely relative. Specifically, a strand synthesized as a complementary strand has the ability to function as a template. In other words, a complementary strand can also serve as a template.

A DNA polymerase catalyzing the complementary strand synthesis reaction that comprises strand displacement is used in the methods for synthesizing or amplifying the polynucleotide the present invention. The same type of polymerases as those used for SDA and such can be used as DNA polymerases of the present invention. A specific polymerase that synthesizes complementary strands by displacing the double-stranded region at the 5' side, if any double-stranded region exists on the template, during complementary strand synthesis using a primer complementary to a region at the 3'-side of a certain nucleotide sequence as the synthesis origin, is known in the art. Thus, the 5'-side of the template is the direction in which the reaction of complementary strand synthesis proceeds. In the present invention, substrates required for complementary strand synthesis are further added.

A DNA polymerase catalyzing a complementary strand synthesis reaction accompanying strand displacement plays a central role in a method for synthesizing a polynucleotide of the present invention. Such DNA polymerases include those listed below. In addition, various mutants of these enzymes can be used in the present invention, so long as they have the activity of sequence-dependent complementary strand synthesis and the strand displacing activity. Such mutants include truncated enzymes having only the structures with catalytic activity or mutant enzymes whose catalytic activity, stability, or thermal stability has been modified by amino acid mutations, and such.

Bst DNA polymerase
Bca(exo-) DNA polymerase
Klenow fragment of DNA polymerase I
Vent DNA polymerase
Vent(Exo-) DNA polymerase (exonuclease activity-free Vent DNA polymerase)
DeepVent DNA polymerase
DeepVent(Exo-) DNA polymerase (exonuclease activity-free DeepVent DNA polymerase)
Φ29 phage DNA polymerase
MS-2 phage DNA polymerase
Z-Taq DNA polymerase' (Takara Shuzo)
KOD DNA polymerase (TOYOBO)

Among these enzymes, Bst DNA polymerase and Bca (exo-) DNA polymerase are particularly preferred, because they are enzymes with thermal stability to a certain degree and high catalytic activity. In the present invention, particularly when using a double-stranded polynucleotide as a template, the annealing of a primer and complementary strand synthesis are conducted under the same conditions. Since such reactions often require some heating, the use of thermostable enzymes is preferred. The reaction can be achieved under a wide variety of conditions by thermostable enzymes.

For example, Vent(Exo-) DNA polymerase is a highly thermostable enzyme that has strand displacing activity. It has been reported that the addition of a single strand-binding protein accelerates the reaction of complementary strand synthesis by DNA polymerase which comprises strand displacement (Paul M. Lizardi et al., Nature Genetics 19, 225-232, July, 1998). By applying the method to the present invention, acceleration of complementary strand synthesis is expected by the addition of a single strand-binding protein. When Vent(Exo-) DNA polymerase is used, T4 gene 32 is effective as the single strand-binding protein.

DNA polymerases lacking 3'-5' exonuclease activity is known to have a phenomenon where the complementary strand synthesis is not terminated even when the reaction reaches the 5'-end of the template and synthesis goes on until an extra nucleotide is added to the synthesized strand. Such a phenomenon is not preferable in the present invention, because the next complementary strand synthesis initiates from the synthesized 3'-end complementary strand sequence. However, the nucleotide added to the 3'-end by the DNA polymerase will be nucleotide "A" with a high probability. Thus, a sequence for complementary strand synthesis should be selected so as to initiate synthesis from the 3'-end from A to avoid problems by the erroneous addition of a single-dATP nucleotide. Alternatively, even when the 3'-end protrudes during complementary strand synthesis, it can be digested to a blunt end by a 3'→15' exonuclease activity. For example, the natural Vent DNA polymerase, which has such a activity, can be used in combination with Vent(Exo-) DNA polymerase to overcome the problem.

Unlike the DNA polymerases described above, DNA polymerases such as Taq polymerase that are routinely used in PCR and such, exhibit substantially no strand displacement activity under usual conditions. However, such DNA polymerases can also be used for the present invention, when they are used under conditions ensuring strand displacement.

Moreover, the present invention relates to a polynucleotide detection method based on the above polynucleotide amplification methods. Namely, the amount or presence of a target nucleotide sequence can be determined by using the amount or presence of products according to the above amplification methods as indexes. Methods for detecting polynucleotides are known. For example, an intercalator like ethidium bromide (abbreviated as EtBr) emits fluorescence by reacting with double-stranded DNA. The amount or presence of a product of an amplification reaction based on the present invention can be determined by using this type of indexes.

The following method, for example, can be used to determine the amount of a polynucleotide based on a polynucleotide detection method of the present invention. To begin with, a method can be used that measures the time required to impart a fixed signal. Since the amplification methods of the present invention are volume-dependent reactions, the time until the reaction reaches a plateau is influenced by the initially present amount of the polynucleotide serving as a template. Thus, provided other reaction conditions are the same, the amount of a polynucleotide can be expressed as a function of the time until the reaction reaches a plateau. In addition, the abundance of a polynucleotide can also be expressed as a function of the amplification product amount formed in a fixed reaction time.

In the LAMP method, an advanced amplification reaction takes place when the region to which the primer of a target nucleotide sequence is to anneal is in a suitable positional relationship, and its nucleotide sequence is as designed. In other words, the LAMP method is considerably inhibited when the target nucleotide sequence is different from the predicted nucleotide sequence in the region that must serve as a starting point for complementary strand synthesis. Complementary strand synthesis in which a 3'-end that anneals to itself serves as the starting point is particularly important. In the LAMP method, a 3'-end that anneals to itself is equivalent to a 3'-end of a complementary strand synthesized by using as a template, a nucleotide sequence arranged on the 5'-end of a primer. Thus, it is preferable to arrange a nucleotide complementary to a mutated site to be detected on the 5'-end or its vicinity of a region (R1 or F1) arranged on the 5'-side of a first primer (RA) and/or second primer (FA) Therefore, if designed so that this important sequence corresponds to a mutation to be detected, the presence of mutations such as nucleotide deletions or insertions, or genetic polymorphisms such as SNPs can be analyzed by observing the amplification reaction product according to the LAMP method.

More specifically, a nucleotide for which a mutation or polymorphism is predicted is designed so as to be equivalent to the vicinity of the 3'-end that serves as the starting point for complementary chain synthesis (or the vicinity of the 5'-end when the complementary strand is the starting point). Namely, it is designed so that, when any nucleotide is different from the predicted nucleotide in a region to which a primer or 3'-end complementary to itself anneals, complementary strand synthesis using that primer as a starting point is impaired. For example, in the case where there is a mismatch within 10 nucleotides from the 3'-end, particularly in the 2nd to 4th nucleotides counting from the 3'-end, and more preferably in the 2nd or 3rd nucleotides counting from the 3'-end, which serves as a starting point for complementary strand synthesis, complementary strand synthesis is significantly inhibited. Here, the predicted nucleotide sequence may be a wild type sequence or a mutated sequence. In the case where a mutated sequence is predicted, complementary strand synthesis starts only when there has been a specific mutation. A polynucleotide complementary strand synthesis reaction is significantly inhibited when there is a mismatch in the 3'-end or its vicinity that serves as the starting point for complementary strand synthesis. Thus, when an amplification reaction is not inhibited, it can be judged that the target nucleotide sequence is composed of the predicted nucleotide sequence. Conversely, when the amplification reaction is inhibited and a product is not formed to the same degree as a control, it can be judged that the target nucleotide sequence differs from the predicted nucleotide sequence.

The LAMP method does not lead to an advanced amplification reaction unless the reaction is repeatedly carried out on the end structure of the initial reaction product. Thus, even if synthesis is carried out incorrectly, since complementary strand synthesis that composes the amplification reaction is always inhibited at each stage, advanced amplification does not occur while containing a mismatch. As a result, a mismatch effectively represses the amplification reaction, and ultimately leads to the obtaining of the correct result. In other words, a polynucleotide amplification reaction based on the LAMP method can be said to have a more highly complete nucleotide sequence check mechanism. These characteristics offer advantages that are unlikely to be expected with methods such as the PCR method in which the amplification reaction is simply carried out in two regions. The present applicant has filed a patent application relating to a polymorphism and mutation detection method based on the LAMP method (WO 01/34838).

The present invention provides a method for detecting a mutation in a target nucleotide sequence by applying a loop primer of the present invention wherein, when a specific nucleotide in a target nucleotide sequence is not the predicted nucleotide, at least one complementary strand reaction synthesis selected from complementary strand reactions that use the 3'-ends of an inner primer, loop primer, and the elongation products of these primers as a starting point is impaired, and whether or not a target nucleotide sequence is the predicted nucleotide sequence is detected by using a product of the above amplification reaction as an index. By observing the production of an amplification reaction product formed based on the above complementary strand synthesis reactions, a specific nucleotide can be judged as not being the predicted nucleotide when the production is inhibited compared to when the target nucleotide sequence is the predicted nucleotide sequence.

In order to detect whether or not a specific nucleotide in a target sequence is the predicted nucleotide by applying the LAMP method based on the present invention, when, for example, a complementary strand synthesized by using the 5'-end of an inner primer as template starts complementary strand synthesis by annealing to itself, it should be designed so that the complementary strand synthesis is controlled by the above specific nucleotide. The present invention can also be designed so that a complementary strand synthesis reaction that starts from the 3'-end of an inner primer is regulated. However, in order to take advantage of the characteristics of the LAMP method in which annealing to a template nucleotide sequence is carried out repeatedly, it is preferable to arrange a checking sequence on the 5'-side of the inner primer. In the present invention, a checking sequence refers to a nucleotide sequence that satisfies the following conditions of (a), (b), and (c).

(a) The checking sequence is arranged on the 5'-end of an inner primer, and the 3'-end of the complementary strand synthesized by using its nucleotide sequence as a template serves as a starting point for complementary strand synthesis by annealing to a target nucleotide sequence or its complementary strand.

(b) In the case where the nucleotide to be checked is not the predicted nucleotide, a mismatch occurs when the 3'-end of (a) anneals to a target nucleotide sequence or its complementary strand.
(c) The complementary strand synthesis of (a) is inhibited by the mismatch that occurred in (b).

Namely, the present invention provides a method for detecting whether or not a specific nucleotide in a target nucleotide sequence is the predicted nucleotide by combining with a loop primer of the present invention using the following first primer and second primer as inner primers, wherein at least either of the first primer or second primer comprises a checking sequence on its 5'-side.

A checking sequence refers to a nucleotide sequence in which, when a nucleotide sequence that composes the above specific region is not the predicted nucleotide sequence, a mismatch occurs when the 3'-end of the complementary strand synthesized using the checking sequence as template is annealed to the target nucleotide sequence or its complementary strand, and a complementary strand synthesis reaction that starts by using the 3'-end as a starting point is inhibited by this mismatch.

First primer: The first primer (i) can provide at its 3'-end a starting point for complementary strand synthesis to a region that defines the 3'-side of one of the strands that composes a target nucleotide sequence, and (ii) has on its 5'-side a nucleotide sequence that is complementary to an arbitrary region of the complementary strand synthesis reaction product that uses this primer as a starting point.

Second primer: The second primer has (i) on its 3'-end a nucleotide sequence that is capable of providing a starting point for complementary strand synthesis to a region that defines the 3'-side of a target nucleotide sequence in an elongation product that uses the above first primer as a starting point, and (ii) on its 5'-side a nucleotide sequence that is complementary to an arbitrary region of the complementary strand synthesis reaction product that uses this primer as a starting point.

The location that provides a mismatch based on a difference in a specific nucleotide by using a checking sequence is preferably, for example, within 10 nucleotides from the 3'-end, particularly preferably the 2nd to 4th nucleotides counting from the 3'-end, and more preferably the 2nd or 3rd nucleotide counting from the 3'-end, which serves as a starting point for complementary strand synthesis. In the present invention, a mismatch at this location most effectively inhibits complementary strand synthesis. Here, the predicted nucleotide sequence may be a wild type sequence or mutated sequence. The polynucleotide complementary strand synthesis reaction is significantly inhibited when a mismatch is present in the 3'-end or its vicinity that serves as a starting point for complementary strand synthesis.

Each of the above methods is for checking a specific nucleotide in a target nucleotide sequence by placing a checking sequence on the 5'-side of an inner primer. In the LAMP method, the 3'-end of a complementary strand synthesized by using the nucleotide sequence arranged on the 5'-side of the inner primer as template, is useful for checking a specific nucleotide in a target nucleotide sequence by using the product of the complementary strand synthesis reaction as an index.

Moreover, the present invention provides a method for checking a specific nucleotide in a target nucleotide sequence by using a nucleotide sequence arranged on the 5'-side of not only an inner primer, but also a loop primer. Namely, the present invention provides a method for detecting whether or not a specific nucleotide in a target nucleotide sequence is the predicted nucleotide by using the following first loop primer and/or second loop primer as a loop primer along with the above inner primer comprising a checking sequence. At this time, however, when the loop primer comprises a nucleotide sequence complementary to the previously mentioned arbitrary region arranged on the 5'-side of the inner primer, or when the nucleotide sequence arranged on the 5'-side of the inner primer is a checking sequence, a sequence in which the nucleotide for providing the above mismatch in the checking sequence differs from the checking sequence placed on the 5'-side of the loop primer. When the nucleotide sequence placed on the 5'-side of the inner primer is a checking sequence, a sequence in which the nucleotide for providing the mismatch differs from the checking sequence, may be different for the nucleotide only, or a plurality of nucleotides including the nucleotide may be different.

First loop primer: Provides, between a region derived from a first inner primer in an elongation product of the first inner primer and the above arbitrary region with respect to the first inner primer, a starting point for complementary strand synthesis.

Second loop primer: Provides, between a region derived from a second inner primer in an elongation product of the second inner primer, and the above arbitrary region with respect to the second inner primer, a starting point for complementary strand synthesis.

A major characteristic of a specific nucleotide check mechanism based on the LAMP method is that a complementary strand synthesis reaction that uses a 3'-end annealed to a template or its complementary strand as a starting point occurs repeatedly. Due to this characteristic, differences in nucleotides in the template can be sensitively detected by using the complementary strand synthesis reaction as an index. However, in the LAMP method as well, reactions occur that are not mediated by a checking mechanism. Since reactions not mediated by a checking mechanism yield products that are not produced as a result of checking the nucleotide sequence of the template, such reaction products have the potential to impair judgment of results. Products that cause this reaction gradually accumulate in the reaction system during the course of repeating the amplification reaction according to the LAMP method.

In an analytical method using an amplification reaction as an index, an important condition for a more sensitive detection is creating as a large a difference as possible in the product amount and reaction rate of the amplification reaction between the case when the amplification reaction proceeds and when the reaction is inhibited. However, if numerous reaction products are present that are formed unrelated to a template nucleotide, it becomes difficult to creating a large difference between the two. In other words, there is the risk of a loss of sensitivity of the analytical method that uses the amount of amplification product formed and its rate of formation as indexes.

In the present invention, the use of the 5'-side of a loop primer for checking a specific nucleotide in a target nucleotide sequence has the effect of repressing the products that have the potential to inhibit judgment of such results. The following provides an explanation of the function of a nucleotide sequence arranged on the 5'-side of a loop primer in the present invention.

The nucleotide sequence arranged on the 5'-side of the loop primer provides a 3'-end that serves as the starting point for complementary strand synthesis by annealing to itself in a complementary strand produced by using the primer as template. At this time, complementary strand synthesis that uses that 3'-end as a starting point is inhibited in the case where a specific nucleotide is the predicted nucleotide. The reason for this is as described below.

As was previously stated, in the method of the present invention, a checking sequence arranged on the 5'-side of an inner primer is designed so that, in the case where a specific nucleotide is not the predicted nucleotide in the 3'-end of a complementary strand produced by using it as a template, complementary strand synthesis is inhibited by that mismatch. In other words, the checking sequence of the inner primer is such that a complementary strand synthesis reaction using as a starting point the 3'-end of a complementary strand used for a template, proceeds when a specific nucleotide is the predicted nucleotide. In this method, products resulting from undesirable reactions that end up occurring when a specific nucleotide in a template nucleotide sequence is not the predicted nucleotide, comprise nucleotide sequences that are displaced with nucleotides that differ from the template in which a specific nucleotide is the predicted nucleotide and so forth. This product was produced as a result of passing through the checking mechanism provided by the 3'-end of the complementary strand synthesized by using the checking sequence as a template for some reason. To facilitate the following explanation, in a complementary strand synthesis reaction that uses as a starting point the 3'-end of a complementary strand produced by using the 5'-side of an inner primer as a template, a product in which the above specific nucleotide has been displaced is tentatively referred to as a pseudo product. The formation of pseudo products and new complementary strand synthesis reactions using formed pseudo products as templates should be repressed in the case of analyzing a specific nucleotide.

A specific nucleotide is not the predicted nucleotide in nucleotide sequences that compose pseudo products. In the case of a loop primer, since the reaction proceeds by using a pseudo product as template, the complementary strand synthesis reaction that uses as a starting point the 3'-end of a complementary strand produced by using 5'-side of the loop primer as template, is impaired in the case when a specific nucleotide is not the predicted nucleotide. Ultimately, the complementary strand reaction from the 3'-end that uses a pseudo product as template, is impaired. In this manner, undesirable reactions can be suppressed by using a nucleotide sequence arranged on the 5'-side of the loop primer.

On the other hand, even when a specific nucleotide in a target nucleotide sequence is the predicted nucleotide, a complementary strand synthesis reaction that uses as a starting point the 3'-end of a complementary strand produced by using a nucleotide sequence arranged on the 5'-side of a loop primer as a template, can be inhibited. However, since a complementary strand synthesis reaction that uses the 3'-side of the loop primer as a starting point proceeds unrelated to the nucleotide sequence arranged on its 5'-side, the accelerating reaction effect itself of the loop primer on the LAMP reaction is not inhibited. Moreover, the amount of the above pseudo products produced is only slight in contrast to the large amount of product produced when a specific nucleotide is the predicted nucleotide. What is more, the inhibiting effect of the reaction due to the above-mentioned mechanism, acts on pseudo products. Finally, the differences in the amount of reaction products and production rate are thought to be further enlarged depending on whether or not a specific nucleotide is the predicted nucleotide. The fact that a nucleotide sequence arranged on the 5'-side of a loop primer has the effect of enlarging the above differences is confirmed also in the examples.

Mutations of nucleotides in a target nucleotide sequence can be identified by using a checking mechanism for a specific nucleotide that uses the above-mentioned inner primer and nucleotide sequence arranged on the 5'-side of a loop primer. Thus, the present invention provides a method for determining whether a specific nucleotide in a target nucleotide sequence is the first nucleotide or the second nucleotide, comprising the step of mixing the following elements a) through d) and then incubating under conditions that enable a complementary strand synthesis reaction accompanying strand displacement, and the formation rate and/or formed amount of the amplification product is measured by any one of the primer sets in a) selected from the group consisting of:

a)
  (1): first nucleotide inner primer pair and first nucleotide loop primer pair
  (2): first nucleotide inner primer pair and second nucleotide loop primer pair
  (3): second nucleotide inner primer pair and first nucleotide loop primer pair, and
  (4): second nucleotide inner primer pair and second nucleotide loop primer pair;

wherein, the first nucleotide inner primer pair and the second nucleotide inner primer pair are both primer pairs consisting of the next first inner primer and second inner primer, and in the first nucleotide primer pair, a complementary strand synthesis reaction using as the starting point the 3'-end of the complementary strand synthesized using the 5'-sides of the first inner primer and second inner primer as a template is not inhibited when the specific nucleotide in the target nucleotide sequence is the first nucleotide, but is inhibited when it is the second nucleotide;

in the second nucleotide inner primer pair, a complementary strand synthesis using as the starting point the 3'-end of a complementary strand synthesized using the 5'-sides of the first inner primer and second inner primer as a template is not inhibited when the specific nucleotide in the target nucleotide sequence is the second nucleotide, but is inhibited when it is the first nucleotide;

the first inner primer has (i) on its 3'-end a nucleotide sequence that provides a starting point for complementary strand synthesis to a region that defines the 3'-side of one of the strands that compose a target nucleotide sequence, and (ii) on the 5'-side a nucleotide sequence that is complementary to the arbitrary region of a complementary strand synthesis reaction product that uses this inner primer as an starting point;

the second inner primer has (i) on its 3'-end a nucleotide sequence that provides a starting point for complementary strand synthesis to a region that defines the 3'-side of a target nucleotide sequence in an elongation product that uses the first inner primer as an starting point, and (ii) on the 5'-side a nucleotide sequence that is complementary to the arbitrary region of a complementary strand synthesis reaction product that uses this inner primer as an starting point;

the first nucleotide loop primer pair and the second nucleotide loop primer pair are both pairs consisting of the next first loop primer and second loop primer, and in the first nucleotide loop primer pair, a complementary strand synthesis reaction using as the starting point the 3'-end of the complementary strand synthesized using the 5'-sides of the first loop primer and second loop primer as template is not inhibited when the specific nucleotide in the target nucleotide sequence is the first nucleotide, but is inhibited when it is the second nucleotide;

in the second nucleotide inner primer pair, a complementary strand synthesis reaction using as the starting point the 3'-end of a complementary strand synthesized using the 5'-sides of the first loop primer and second loop primer as a template is not inhibited when the specific nucleotide in the target nucleotide sequence is the second nucleotide, but is inhibited when it is the first nucleotide;

the first loop primer provides, between a region derived from the first inner primer in an elongation product of the first inner primer and the arbitrary region with respect to the first inner primer, a starting point for complementary strand synthesis, and the second loop primer provides, between a region derived from the second inner primer in an elongation product of the second inner primer and the arbitrary region with respect to the second inner primer, a starting point for complementary strand synthesis;

b) a DNA polymerase catalyzing complementary strand synthesis accompanying strand displacement;

c) a substrate for complementary strand synthesis; and d) a test polynucleotide comprising a target nucleotide sequence.

In the explanations of the nucleotide sequences of each of the above primers, inhibition of complementary strand synthesis refers to the occurrence of a mismatch when a specific nucleotide is a certain nucleotide and the impairment of complementary strand synthesis caused by that mismatch when the 3'-end of a complementary strand produced using a nucleotide sequence arranged on the 5'-side of each primer as a template anneals to a region containing a specific nucleotide in the same manner as the checking sequence in an inner primer as previously described. The method for identifying a specific nucleotide of the present invention is useful for identifying nucleotide mutations and polymorphisms. For example, the present invention can be used to determine whether or not a certain nucleotide is the wild type or mutant. In this case, the method of the present invention can be carried out by designing each of the above primers by using either a first nucleotide or second nucleotide as a wild type and using the other as a mutant. As a result, the nucleotide can be identified to be of the wild type or mutant based on the combinations of primer sets when the production rate of the complementary strand synthesis reaction product reaches a maximum and a minimum. More specifically, the production rates of amplification products when a specific nucleotide is of the wild type and when a specific nucleotide is of the mutant, with respect to the following four primer sets of (1) through (4), are the following combinations.

When the target nucleotide sequence is the wild type: (1) is maximum and (3) is minimum When the target nucleotide sequence is a mutant: (4) is maximum and (2) is minimum (1): Wild type inner primer pair and wild type loop primer pair
(2): Wild type inner primer pair and mutant loop primer pair
(3): Mutant inner primer pair and wild type loop primer pair
(4): Mutant inner primer pair and mutant loop primer pair This method is none other than a method for double checking a specific nucleotide. In this manner, the reliability of analysis results of a specific nucleotide in a target nucleotide sequence can be improved by using primer pairs composed of a plurality of primers. In methods for identifying a specific nucleotide based on a known nucleic acid amplification reaction like PCR, there is no known method for enhancing the reliability of analysis results in this manner.

The various types of reagents required for the polynucleotide synthesis method according to the present invention, the amplification method that uses this synthesis method, or method for detecting mutations in a target nucleotide sequence that uses this amplification method, may be provided by prepackaging in a kit. More specifically, a kit is provided for carrying out the present invention that is composed of reagents involving various oligonucleotides required for use as a first primer, second primer, and a loop primer, dNTPs to serve as the substrate of complementary strand synthesis, DNA polymerase for carrying out strand displacement type complementary strand synthesis, and buffers for providing suitable conditions for enzyme reactions. An outer primer may also be combined with the kit of the present invention. The combination of outer primer allows isothermal reactions.

As already described, the polynucleotide amplification reactions of the present invention make it possible to detect target nucleotide sequences. Thus, a polynucleotide amplification reaction kit according to the present invention can be used as a kit for detecting a target nucleotide sequence or as a kit for detecting mutations in a target nucleotide sequence.

Namely, the present invention relates to kits for detecting a target nucleotide sequence that contains the constituent elements described above. Moreover, a kit for detecting mutations in a target nucleotide sequence can be provided by using each of the primers that compose a kit for detecting a target nucleotide sequence of the present invention primers for detecting mutations. In addition to an outer primer, reagents required for detecting synthesis reaction products may be combined with the kit according to the present invention as necessary.

Especially, in a preferable embodiment of the present invention, the reaction can be started simply by adding a sample, by providing a reaction container containing reagents required for a single reaction, since it is not necessary to add reagents during the course of the reaction. If a system is provided that allows detection of the reaction product to be carried out directly in the reaction container by using a luminescent signal or fluorescent signal, the opening of the container after the reaction can be completely eliminated. This is highly desirable in terms of preventing contamination.

BRIEF DESCRIPTION OF THE DRAWINGS

FIG. 4 shows the positional relationship between the template polynucleotide sequence used in the Examples (SEQ ID NO: 1) and the nucleotide sequences of respective primers. The open-faced nucleotides show the annealing site for the loop primers and the arrows indicate the synthesis direction of the complementary strand.

BEST MODE FOR CARRYING OUT THE INVENTION

The present invention will be explained in detail below with reference to examples.

EXAMPLE 1

Accelerating Effect of Loop Primers on Polynucleotide Amplification

1. Design of the Loop Primers

To accelerate polynucleotide amplification by the LAMP method, the effect of adding primers was tested. The design site of the loop primers was set so as not to be within the R2 or F2 regions of loop structures formed during the LAMP reaction. The direction of the primers was same as R1 or F1. (Hereafter they will be described as loop primers). The direction of R1 or F1 indicates the same direction in which the template polynucleotides anneal to themselves to synthesize a complementary strand. First, the following primers for the target sequence (SEQ ID NO: 1) were individually designed according to the known LAMP method (WO 00/28082). The positional relationships between the template polynucleotide sequence (SEQ ID NO: 1) and each primer sequence are shown in FIG. 4. The open-faced nucleotides show the site to which the loop prier anneals and the arrow indicates the direction of complementary strand synthesis.

Inner primer RA (Inner F, SEQ ID NO: 2),
Inner primer FA (Inner R, SEQ ID NO: 3),
Outer primer F (Outer F, SEQ ID NO: 4), and
Outer primer R (Outer R, SEQ ID NO: 5).

The following primers were designed to be the same direction as R1 and F1 that are defined by the above primers.
Loop primer F (Loop F, SEQ ID NO: 6) and
Loop primer R (Loop R, SEQ ID NO: 8).

All primers were synthesized by the known LAMP method.

Figure 1:
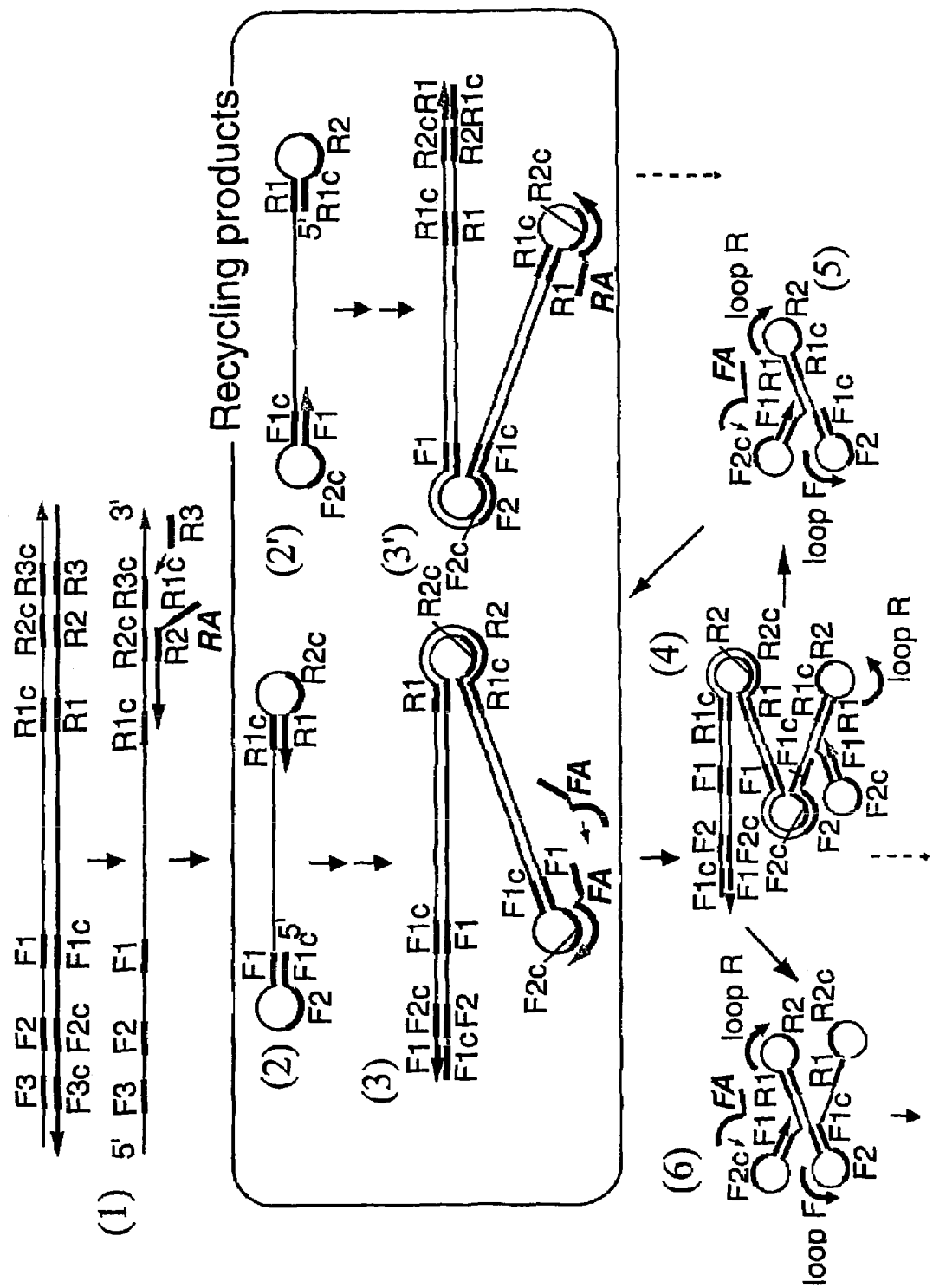
FIG. 1 illustrates the principle of the polynucleotide amplification reaction using the present invention. FA: Primer FA for LAMP method; RA: primer RA for LAMP method; loop F: Loop primer F; loop R: Loop primer R.
Figure 2:
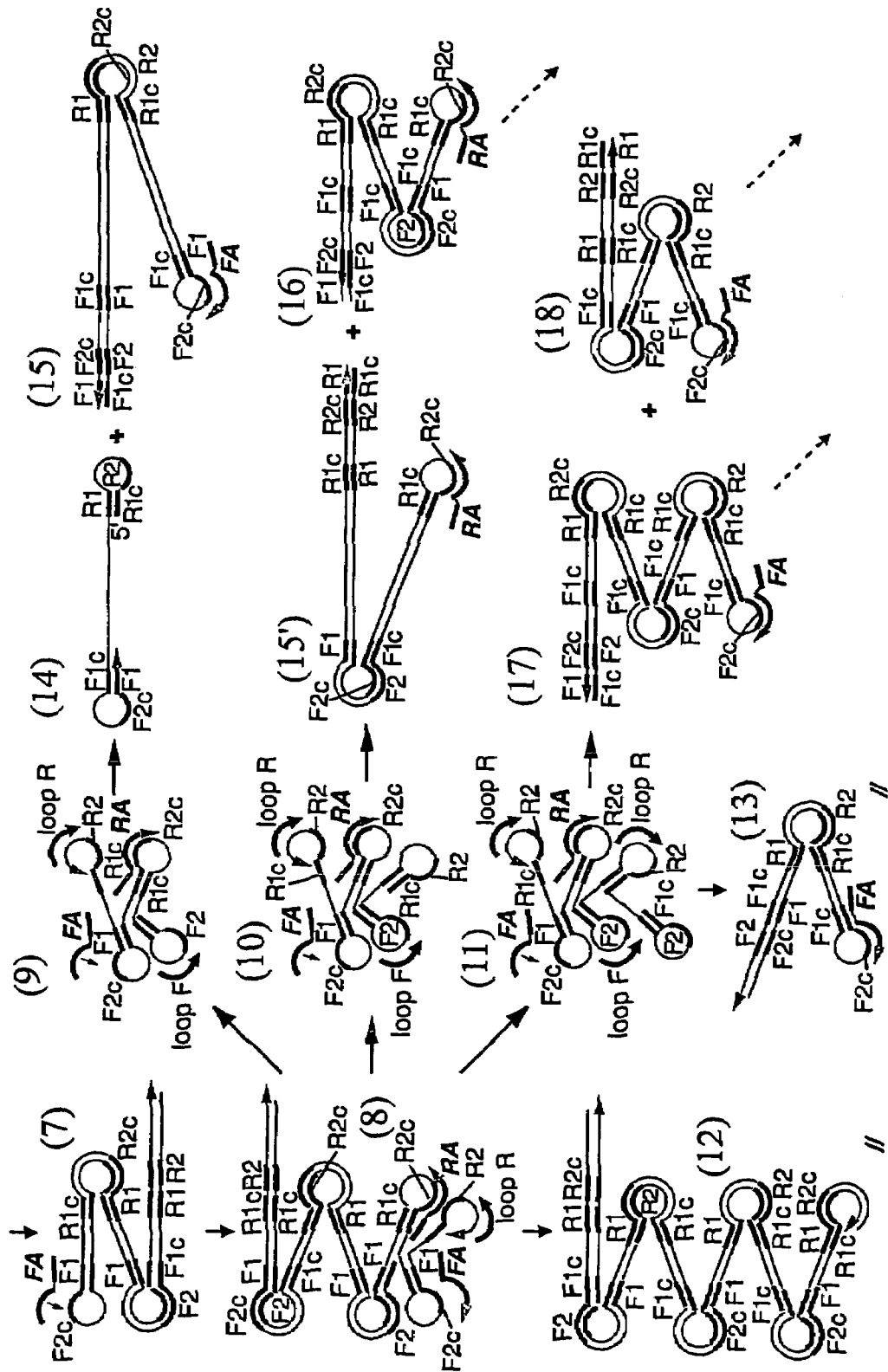
FIG. 2 shows the reaction principle of the polynucleotide amplification method using the invention. Abbreviations used in the figure are the same as in FIG. 1.

By using loop primers, in addition to the reactions of the known LAMP method, one can expect another amplification reaction to occur, which is expected to accelerate the amplification reaction (FIGS. 1 and 2).

2. Effect of Loop Primers

The LAMP reaction was carried out according to the reaction conditions described below using λDNA ($1 \times 10^5$ molecules) as template. Non-heat-denatured λDNA was prepared. The reaction was carried out at 65° C. using the sequence detection system ABI PRISM 7700 (Perkin-Elmer Biosystems) and the transition of reaction was periodically monitored.

Figure 5:
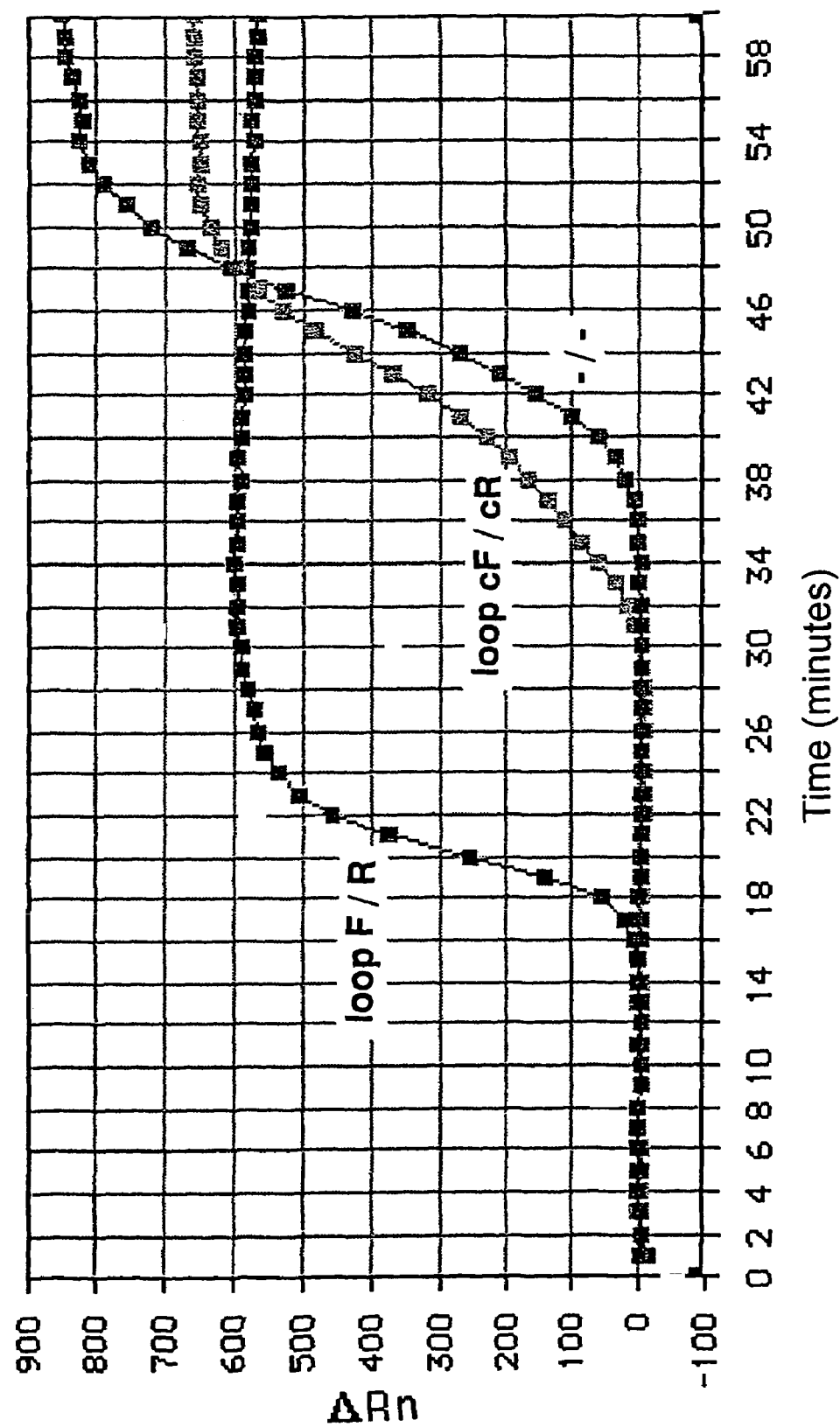
FIG. 5 shows the accelerating effect of loop primers on the polynucleotide amplification reaction. The X-axis indicates the reaction time and the Y-axis indicates the change in fluorescence intensity (ΔRn). Loop F/R: loop primer R and loop primer F were used. Loop cF/cR: loop cF and loop cR consisting of the complementary sequences of loop primers F and R were used. −/−: loop primers were not added.

Reaction composition (in 25 μl)
20 mM Tris-HCl pH 8.8
10 mM KCl
10 MM $(NH_4)_2SO_4$
4 mM $MgSO_4$
1-M Betaine
0.1% Triton X-100
0.4 mM dNTP
8 U Bst DNA Polymerase (NEW ENGLAND BioLabs)
0.25 μg/ml EtBr Primers:
 1600 nM Inner F
 1600 nM Inner R
 400 nM Outer F
 400 nM Outer R SEQ ID NO: 1 is the target nucleotide sequence (λDNA 1) of λDNA. Loop primers were simultaneously added to the final concentration of 400 nM. Consequently, a reaction accelerating effect was observed in the reaction system to which loop primers were added. On the other hand, primers consisting of complementary strands of loop primers (Loop cF/SEQ ID NO: 7 and Loop cR/SEQ ID NO: 9), had no effect (FIG. 5).

Figure 6:
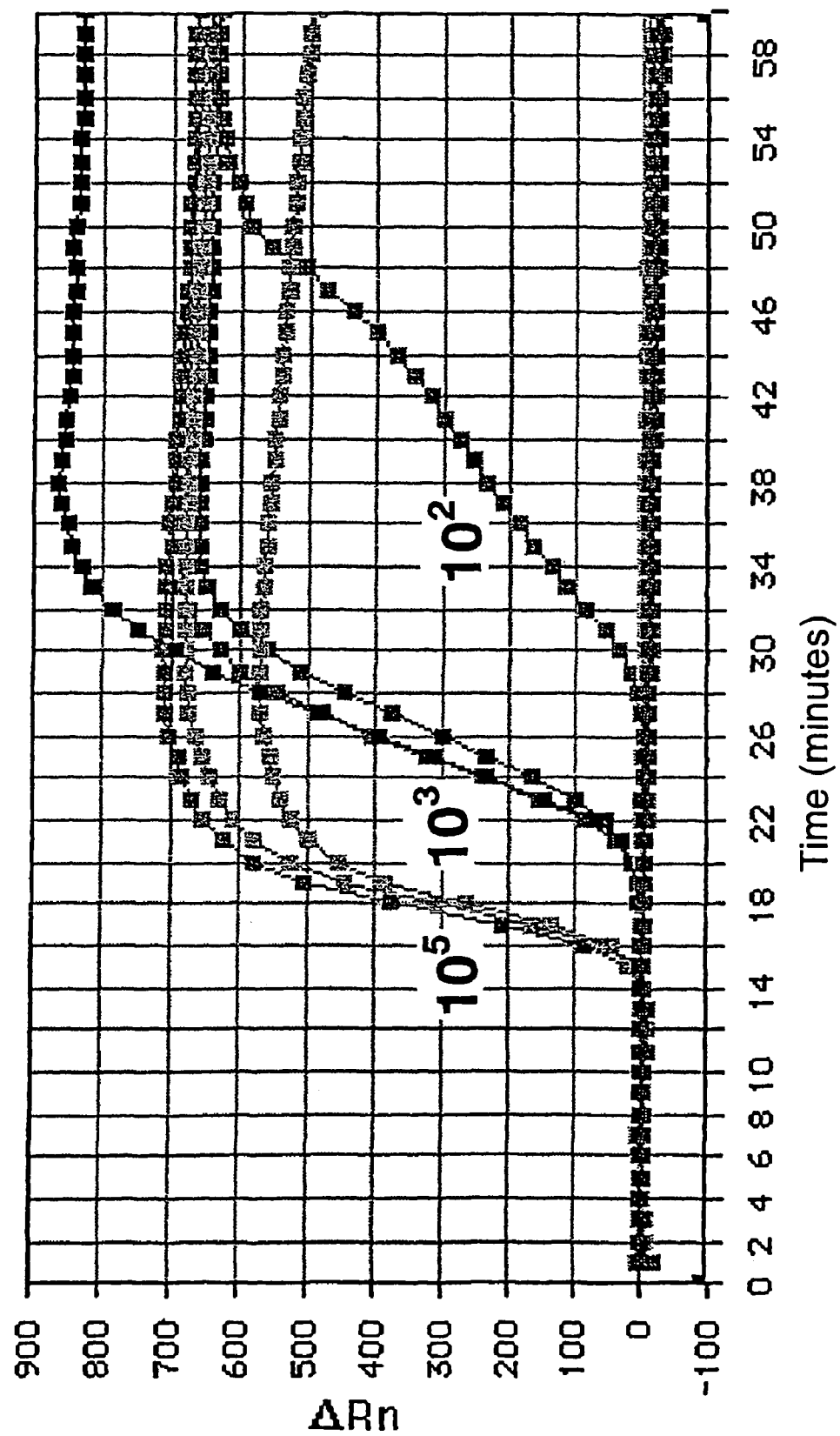
FIG. 6 shows the result of evaluating the amount of added template DNA and the amplified products. The X-axis indicates the reaction time and the Y-axis indicates the change in fluorescence intensity (ΔRn).

Various concentrations of λDNA ($1\times10^2$, $1\times10^3$, $1\times10^5$ molecules) were used as templates in the presence of loop primers to evaluate the detection limit. As a result, reproducible results were obtained when up to $1\times10^3$ molecules of the templates were used (FIG. 6). In the absence of loop primers, even $1\times10^5$ molecules of template DNAs gave variable results (data not shown), indicating that amplification of a low amount of template can be accomplished by using loop primers.

2. Concentration Dependency of Loop Primers

Figure 7:
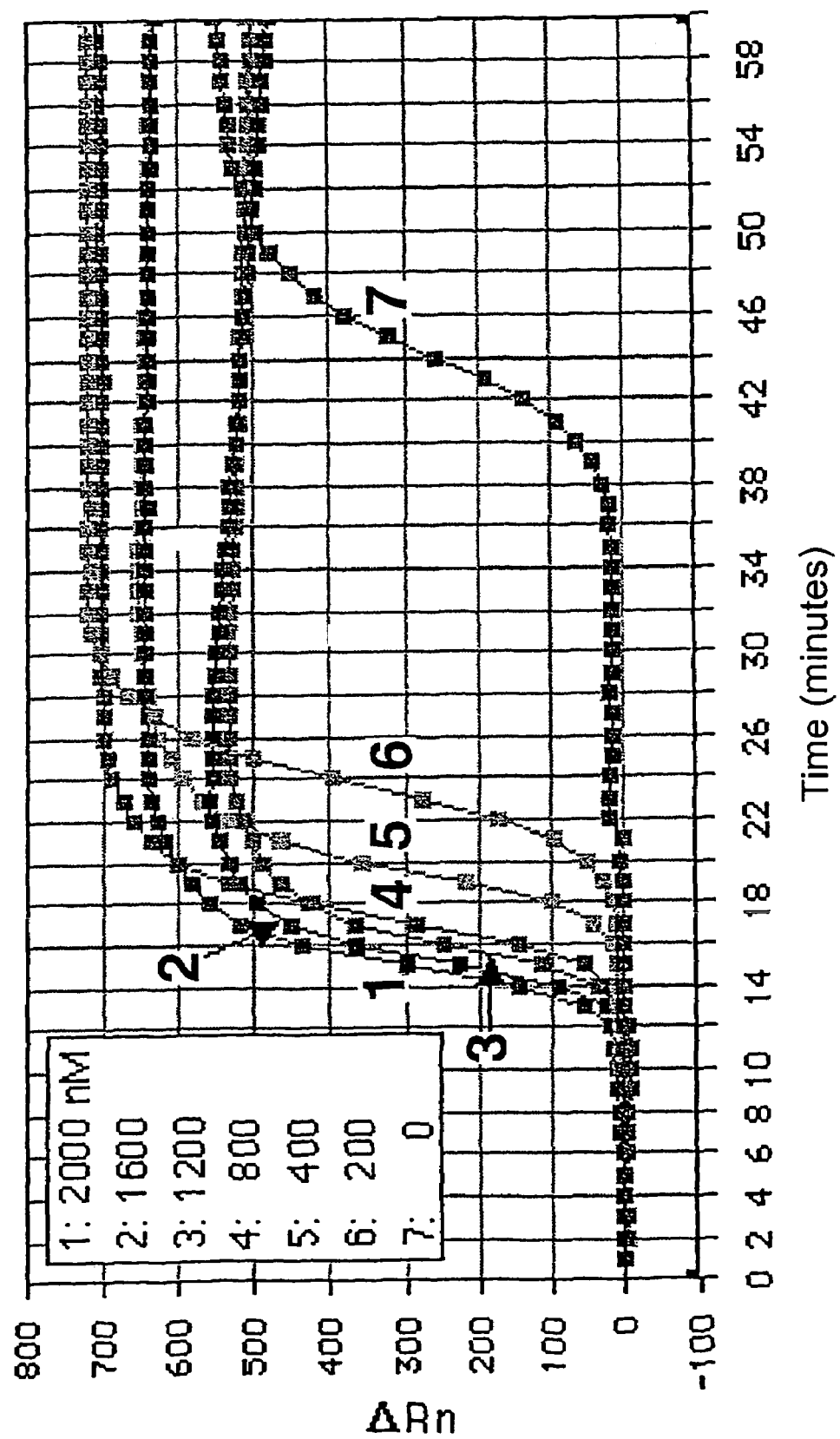
FIG. 7 shows the concentration dependency of loop primers. The X-axis indicates the reaction time and the Y-axis indicates the change in fluorescence intensity (ΔRn).

Loop primers at final concentrations of 200, 400, 800, 1200, 1600, and 2000 nM were added to the LAMP reaction system to test the effect of changing loop primer concentration on the LAMP reaction. Consequently, as loop primer concentration increased, acceleration of the LAMP reaction was observed (FIG. 7). A final concentration of 800 nM loop primers was used in the examples hereafter.

3. Effect of 3' Modified Loop Primers on the LAMP Reaction

Figure 8:
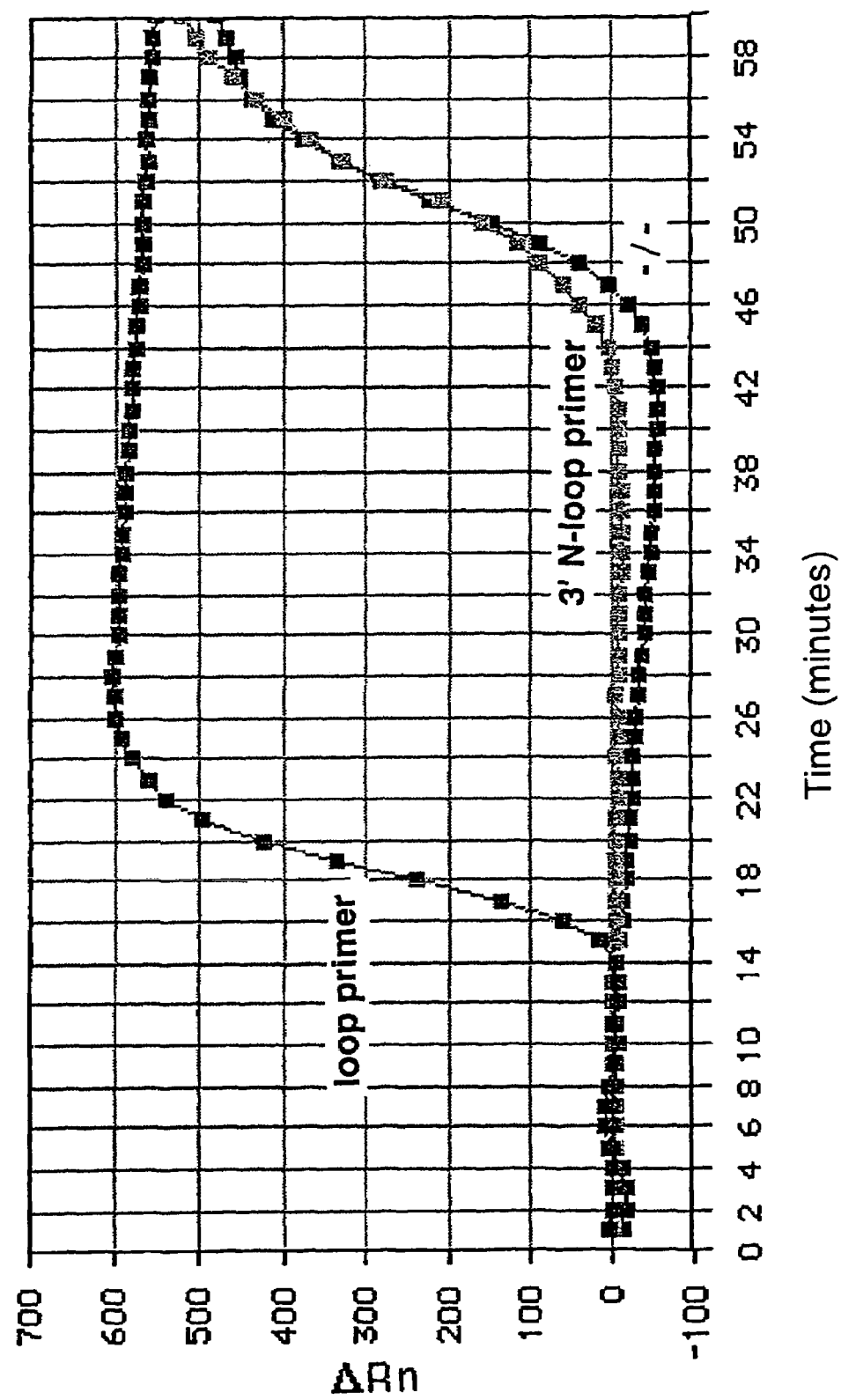
FIG. 8 shows the effect of a 3'-aminated loop primer. The X-axis indicates the reaction time and the Y-axis indicates the change in fluorescence intensity (ΔRn). Loop primer: a Loop primer with an unmodified 3' end was used. 3' N-loop primer: Loop primer with an aminated 3' end was used. −/−: a loop primer was not added.

To inhibit the extension reaction from a loop primer, a loop primer aminated at the 3' end was prepared. The aminated loop primer was added to the LAMP reaction at a final concentration of 800 nM to test the accelerating effect. The result showed that in the presence of the aminated loop primer, no acceleration of reaction was observed. This indicated that the extension reaction from the loop primer is involved in the acceleration of the LAMP reaction (FIG. 8).

4. Effect of Outer Primers

Figure 9:
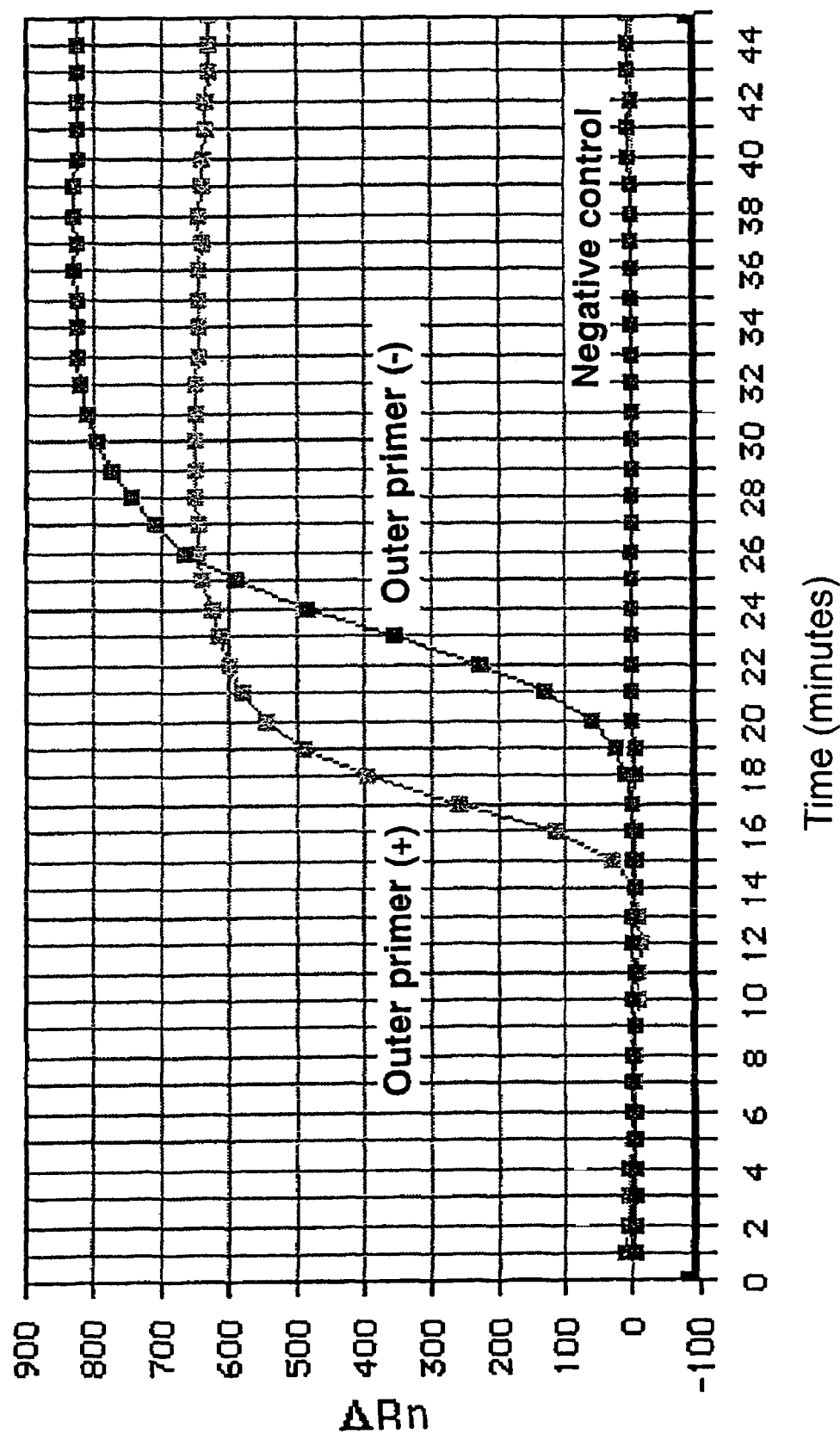
FIG. 9 shows the effect of the presence or absence of outer primers on polynucleotide amplification. The X-axis indicates the reaction time and the Y-axis indicates the change in fluorescence intensity (ΔRn). Outer primer (+): presence of outer primer. Outer primer (−): absence of outer primer. Negative Control: template cDNA not added.

The effect of the absence or presence of outer primers on LAMP reaction was tested in the presence of loop primers. In the absence of outer primers, there was a 10-minute reaction delay (FIG. 9). This result indicated that the combination of outer primers with loop primers was also advantageous in further accelerating the reaction.

5. Effect of Loop Primer Tm

The effect of loop primer Tm was tested by shortening the 5' end of primers. Loop primers used in the experiments are as follows:

Loop primer F–1 lacking one nucleotide (Loop F–1, SEQ ID NO: 10);
Loop primer R–1 lacking one nucleotide (Loop R–1, SEQ ID NO: 12);
Loop primer F–2 lacking two nucleotides (Loop F–2, SEQ ID NO: 11); and
Loop primer R–2 lacking two nucleotides (Loop R–2, SEQ ID NO: 13).

Figure 10:
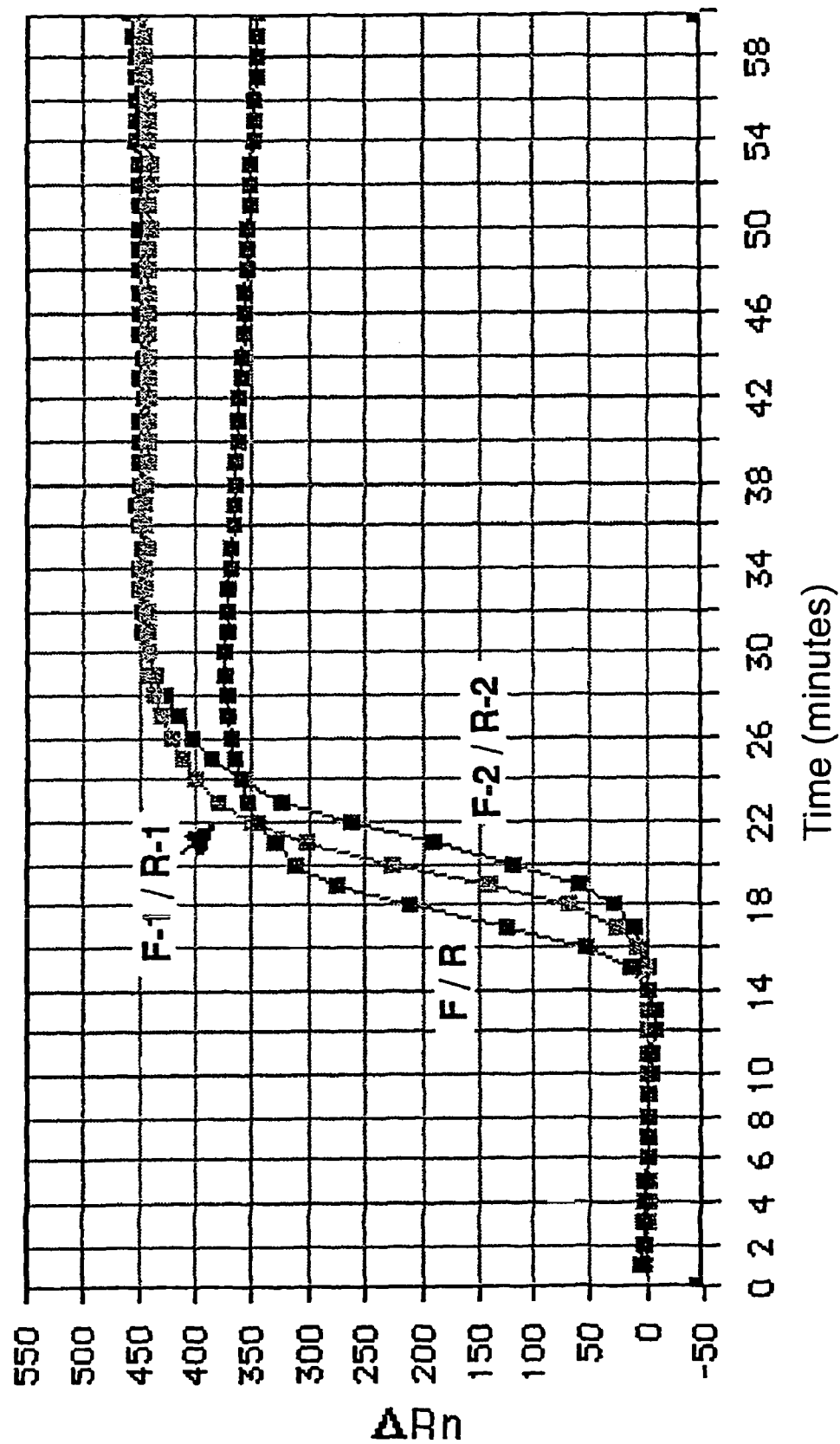
FIG. 10 shows the result of evaluating primer length. The X-axis indicates the reaction time and the Y-axis indicates the change in fluorescence intensity (ΔRn). F/R: loop primers R and F were used. F−1/R−1: loop primers F and R with 1 nucleotide less at the 5'end were used. F−2/R−2: loop primers F and R with 2 less nucleotides at the 5'end were used.

As a result of using these primers, the rate of reaction slowed down when primers lacking one nucleotide were used, and the rate was further reduced when primers lacking two nucleotides were used (FIG. 10). It was suggested that the reduction of reaction rate was due to the decrease of loop primer Tm that made the reaction more difficult at 65° C.

6. Effect of Loop Primer Design Site

To evaluate the loop primer design site, new primers were designed in a different region of λDNA. The sequence of the target nucleotide sequence (λDNA2) is shown as SEQ ID NO: 14. Following LAMP primers were designed to amplify the target nucleotide sequence.
Inner primer RA (Inner F, SEQ ID NO: 15),
Inner primer FA (Inner R, SEQ ID NO: 16),
Outer primer F (Outer F, SEQ ID NO: 17), and
Outer primer R (Outer R, SEQ ID NO: 18).

Then the following primers were designed to be the same direction as R1 and F1 that are defined by above primers.
Loop primer F3: No overlapping with the R2 region (Loop F3, SEQ ID NO: 19)
Loop primer R4: No overlapping with the F2 region (Loop R4, SEQ ID NO: 20)
Loop primer F5: 3 nucleotides overlapping with the R2 region (Loop F5, SEQ ID NO: 21)
Loop primer R5: 3 nucleotides overlapping with the F2 region (Loop R5, SEQ ID NO: 22)
Loop primer F6: 3 nucleotides overlapping with the R1 region (Loop F6, SEQ ID NO: 23)
Loop primer R6: 3 nucleotides overlapping with the F1 region (Loop R6, SEQ ID NO: 24)
Loop primer F7: 10 nucleotides overlapping with the R1 region (Loop F7, SEQ ID NO: 25)
Loop primer R7: 10 nucleotides overlapping with the F1 region (Loop R7, SEQ ID NO: 26)
Loop primer F8: completely overlapping with the R1 region (Loop F8, SEQ ID NO: 27)
Loop primer R8: completely overlapping with the F1 region (Loop R8, SEQ ID NO: 28)

Figure 11:
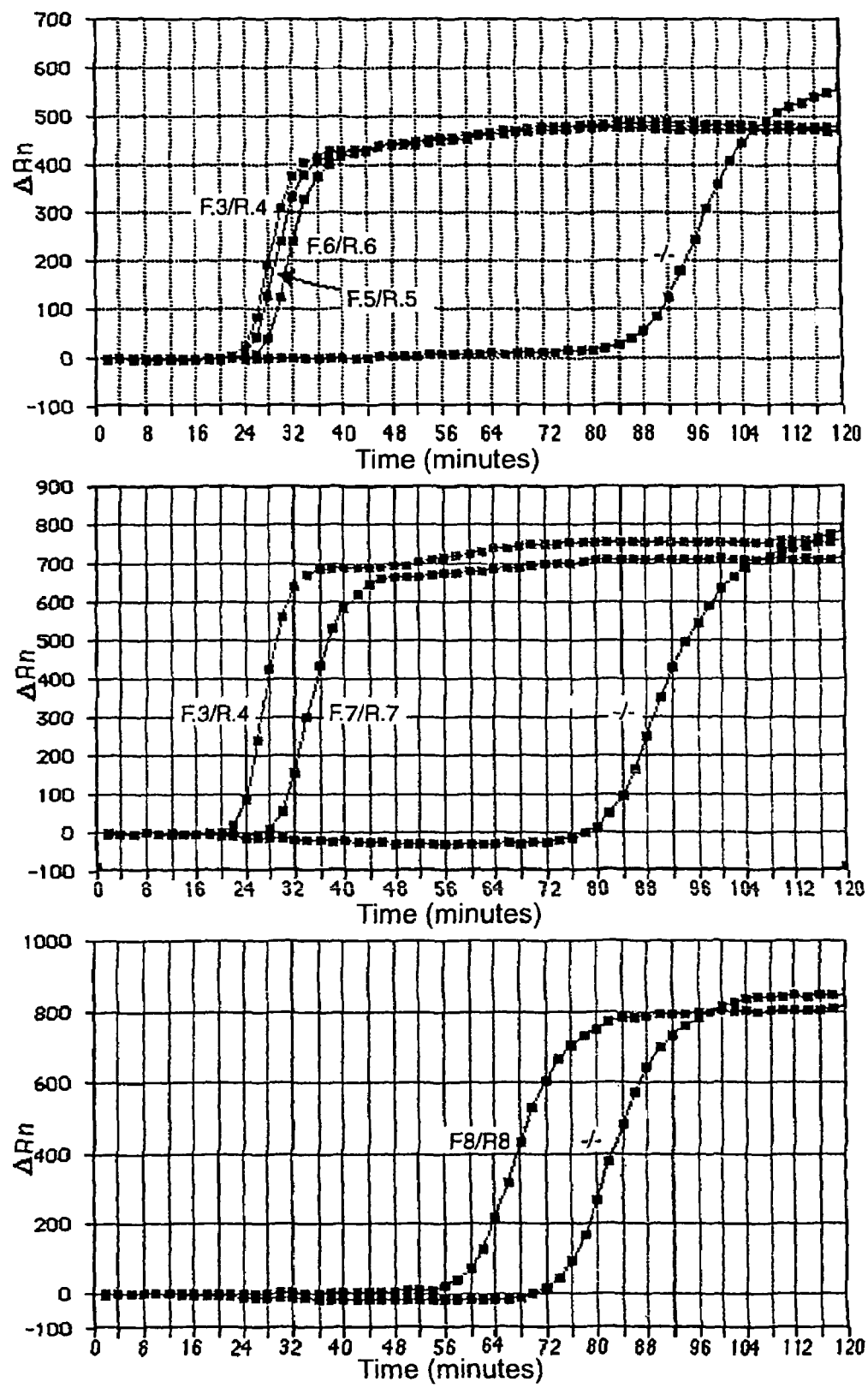
FIG. 11 shows the result of evaluating loop primer design site. The X-axis indicates the reaction time and the Y-axis indicates the change in fluorescence intensity (ΔRn). F3/R4: loop primers F3 and R4 that do not overlap with the F2 and R2 regions, respectively, were used. F5/R5: loop primers F5 and R5 overlapping 3 nucleotides with the F2 and R2 region, respectively, were used. F6/R6: loop primers F6 and R6 overlapping 3 nucleotides with the F1 and R1 regions, respectively, were used. F7/R7: loop primers F7 and R7 overlapping 10 nucleotides with the F1 and R1 regions, respectively, were used. F8/R8: loop primers F8 and R8 completely overlapping with the F1 and R1 regions, respectively, were used. −/−: loop primers were not added.

The presence or absence of overlappings with the R2 and F2 regions did not affect the reaction rate, and there was no difference in reaction rate among these loop primers. The primers in which 3 nucleotides overlapped with the R1 (or F1) region (loop F6/loop R6) were also used, but did not affect the reaction rate (FIG. 11).

Figure 3:
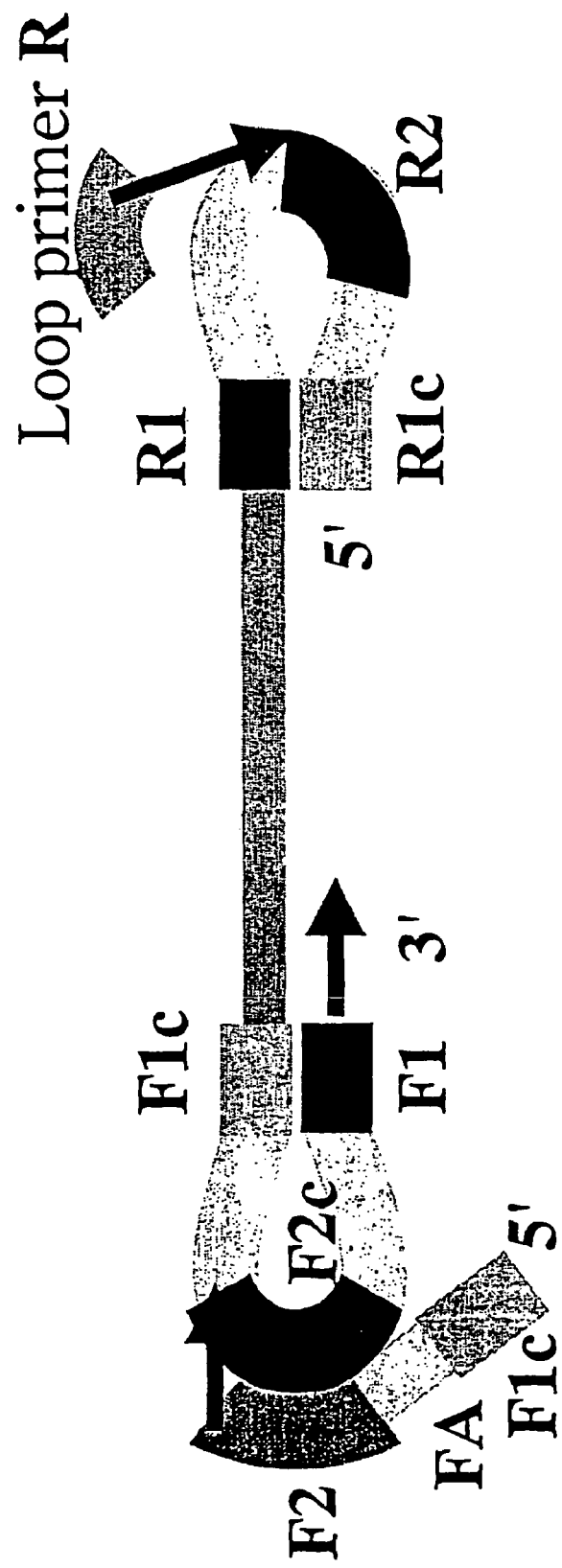
FIG. 3 shows the preferable positional relationship between loop primers and the sequence of the template polynucleotide.

Moreover, primers having a 10-nucleotide overlap in the R1 (or F1) region (loop F7/loop R7) were prepared. Although, the reaction rate slowed down with this setting compared to when there were 3 or less overlappings, an accelerating effect was still observed (FIG. 11). For primers that completely overlapped with the R1 (or F1) region (loop F8/loop R8), an accelerating effect was observed compared to the reaction without the loop primers (FIG. 11). The reasons for the reduction of the reaction rate may be the competitive inhibition in the R1 (or F1) region that made it more difficult to form the dumbbell-like structure (FIG. 3), and the fact that primers had to anneal to the R1 region that became double-stranded.

EXAMPLE 2

SRY Gene Amplification

The effect of loop primers on the LAMP reaction using human genome as template was tested. The SRY gene mapped on the Y chromosome was selected as a target gene. The target nucleotide sequence is shown in SEQ ID NO: 29. To amplify the target nucleotide sequence, the following LAMP were designed.
Inner primer RA (Inner F, SEQ ID NO: 30)
Inner primer FA (Inner R, SEQ ID NO: 31)
Outer primer F (Outer F, SEQ ID NO: 32), and
Outer primer R (Outer R, SEQ ID NO: 33).

Then, the following loop primers were designed to be the same direction as R1 and F1 that were defined by the above primers.
Loop primer F (Loop F, SEQ ID NO: 34) and
Loop primer R (Loop R, SEQ ID NO: 35).

Figure 12:
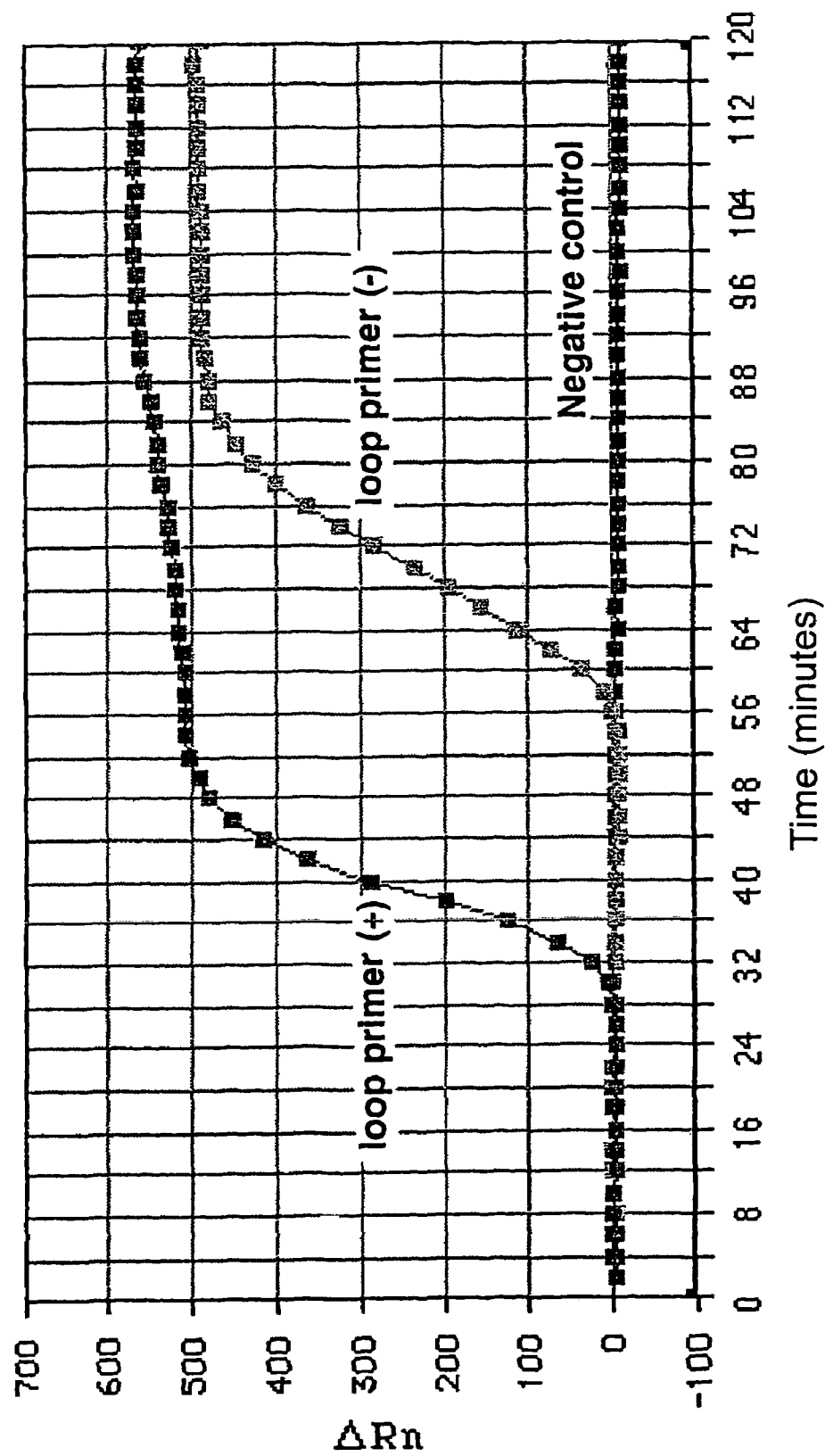
FIG. 12 shows the result of SRY gene amplification according to the present invention. The X-axis indicates the reaction time and the Y-axis indicates the change in fluorescence intensity (ΔRn). Loop primer (+): presence of Loop primer. Loop primer (−): absence of loop primer. Negative Control: template DNA not added.

The LAMP reaction was carried out using 100 ng of human genome. Consequently, it was confirmed that the reaction was accelerated when the loop primers were added (FIG. 12). That is, from this experiment, the accelerating effect of loop primers on the LAMP reaction was confirmed even when the human genome was used as template. It was indicated that rapid genome analysis such as the detection of SNPs could be done based on the present invention.

EXAMPLE 3

Loop Primers with a Nucleotide Sequence Added to their 5' Side

Figure 13:
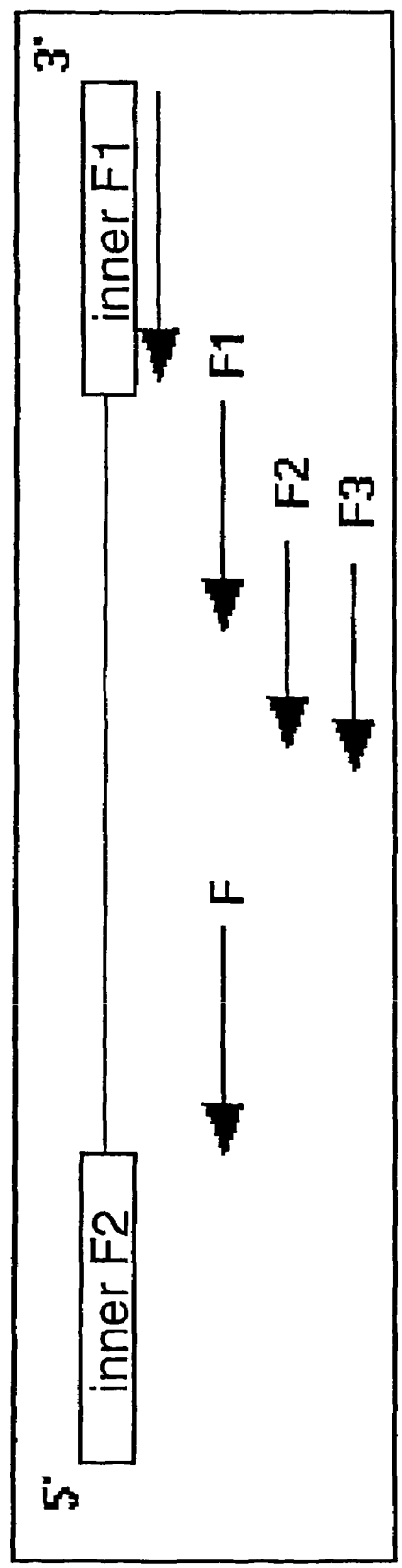
FIG. 13 shows the positional relationship between loop primer added to the 5' end and the template nucleotide sequence. "c" means complementary sequence.

The acceleration of reaction rate was confirmed when a nucleotide sequence complementary to an arbitrary region of the complementary strand synthesized from the 3' end of a loop primer was added to the 5' side of the loop primer. The template used in this experiment was the same λDNA (λDNA2) as described in Example 1. The reaction conditions were also the same as in Example 1. First, primers F9-F15 were designed as shown in FIG. 13. At the 5' side of the loop primers, various nucleotide sequences were added. The following is a list of nucleotide sequences that were added to the 5' side.

| Loop primer Sequence at 5' side | Sequence at 3' side |
|---|---|
| F9  inner F1 | F3 |
| F10 F1 | F |
| F11 F1 | Fc |
| F12 F | F1 |
| F14 inner F1c | F2 |
| F15 inner F1 | F1 |

The positional relationship of each nucleotide sequence constituting the above mentioned loop primers relative to the template nucleotide sequence are as shown in FIG. 13. Each nucleotide sequence is briefly described below. Nucleotide sequence with a "c" means a complementary sequence.

The following explanation describes each regions of the loop that include the nucleotide sequence of inner primer FA. However, in the experiment, the same loop primers were also designed for loops that include the inner primer RA sequence, and used. The primer sequences actually used in the experiment are described at the end.

Inner F1: complementary nucleotide sequence of F1c located at the 5' side of inner primer FA.

F1: Region adjacent to the 5' side of inner F1 in the loop.

F2: Region partly overlapping with F1 in the loop and its 3' end located closer towards the 5' side than F1.

F3: Region partly overlapping with F1 in the loop and its 3' end located closer towards 5' side than F2.

F: Region adjacent region where inner primer F2c anneals in the loop.

The LAMP reaction was carried out using these loop primers, and it was shown that the reaction was accelerated compared to the reaction without loop primers.

Figure 14:
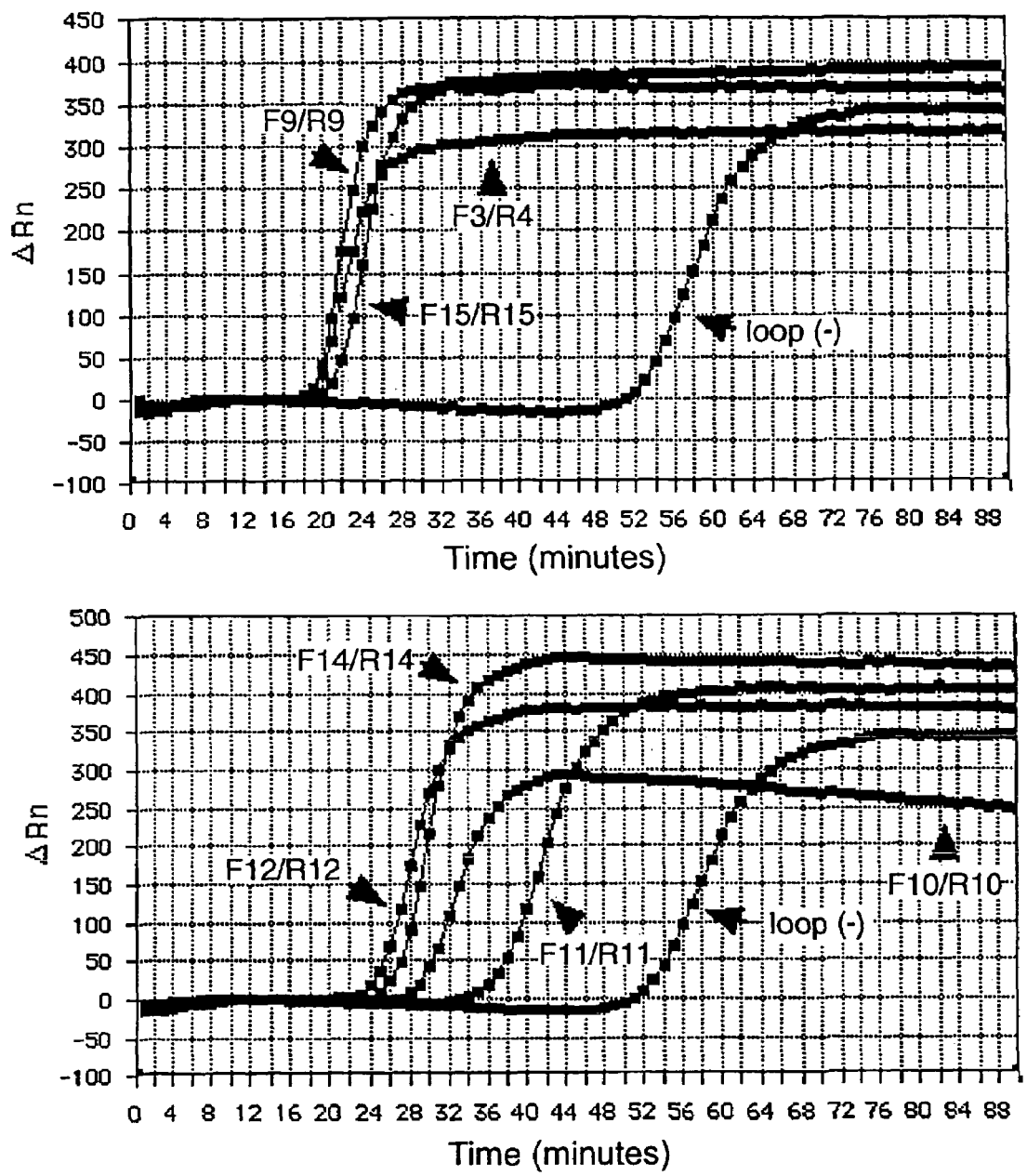
FIG. 14 shows the accelerating effect of the loop primer added to the 5' end. The X-axis indicates the reaction time and the Y-axis indicates the change in fluorescence intensity (ΔRn).

In the previous experiment, it was demonstrated that the loop primer that hybridizes to the loop to which the inner primer binds (loop CF/CR), does not have an effect on this reaction (FIG. 5). In this experiment, as shown in FIG. 14, the accelerating effect of the LAMP reaction was observed with the primer combination of F11/R11. At the 5' side of F11 and R11, primers have structures having nucleotide sequences complementary to arbitrary regions of the complementary strand extended from their 3' ends. This structure is the so-called inner primer structure. Therefore, it was thought that the complementary strand that was synthesized using the loop primer as template, has a structure that causes the next extension reaction to occur using itself as template.

The following are the primer sequences used in this experiment:

```
F9/   CGTGAGCAATGGGTATATGCAAATGGAACTCCGGGTGCTATCAG/      SEQ ID NO:36

R9/   ATGTCCTTGTCGATATAGGGATGAATGACCTTTCTCTCCCATATTGCAGTCG/   SEQ ID NO:37

F10/  TTCGTTTCCGGAACTCCGGGTTGAATGCCCGGCGAACTGGAG/       SEQ ID NO:38

R10/  TCGCTTGGTGTACCTCATCTACTGCGGCAGTCGCGGCACGATGGAACTA/   SEQ ID NO:39

F11/  TTCGTTTCCGGAACTCCGGGTCTCCAGTTCGCCGGGCATTCA/       SEQ ID NO:40

R11/  TCGCTTGGTGTACCTCATCTACTGCGTAGTTCCATCGTGCCGCGACTGC/   SEQ ID NO:41

F12/  CTCCAGTTCGCCGGGCATTCATTCGTTTCCGGAACTCCGGGT/       SEQ ID NO:42

R12/  TAGTTCCATCGTGCCGCGACTGCTCGCTTGGTGTACCTCATCTACTGCG/   SEQ ID NO:43

F13/  TCCAGTTCGCCGGGCATTGTTTCCGGAACTCCGGGT/           SEQ ID NO:44

R13/  TAGTTCCATCGTGCCGCGACTTCGCTTGGTGTACCTCATCTACTG/      SEQ ID NO:45

F14/  ATTTGCATATACCCATTGCTCACGGGAACTCCGGGTGCTATCAG/      SEQ ID NO:46

R14/  TTCATCCCTATATCGACAAGGACATTGACCTTTCTCTCCCATATTGCAGTCG/ SEQ ID NO:47

F15/  CGTGAGCAATGGGTATATGCAAATTTCGTTTCCGGAACTCCGGGT/     SEQ ID NO:48

R15/  ATGTCCTTGTCGATATAGGGATGAATCGCTTGGTGTACCTCATCTACTGCG/ SEQ ID NO:49
```

EXAMPLE 4

Detection of a Mutation with a Nucleotide Sequence Placed at the 5' Side of a Loop Primer By utilizing a nucleotide sequence placed at the 5' side of loop primers of the present invention, it was confirmed that when a specific nucleotide in the target nucleotide sequence was not the predicted one, the polynucleotide amplification method according to the present invention was inhibited. Therefore, by monitoring the presence or absence of a reaction inhibition, one can detect a mutation of a specific nucleotide.

At the 5' side of a loop primer used for this experiment, the nucleotide sequence same as the one placed in the 5' side of the inner primer was placed. That is, in the 5' side of loop primer F, a nucleotide sequence of the 5' side of inner primer FA was placed. The 5' side of loop primer R was designed to have the nucleotide sequence of the 5' side from the inner primer RA. Moreover, in the 5' end of each primer, primers comprising nucleotides complementary to a mutant sequence (MT) and wild-type sequence (WT) were prepared, and for all combinations of primers, the amplification reactions based on the present invention were performed. When an amplification reaction based on the present invention is conducted using these primers, a complementary strand is synthesized using each loop primer as template. Then when the complementary strand anneals to itself to start complementary strand synthesis, a specific nucleotide can be distinguished. In other words, the 3' end of a complementary strand synthesized using a primer (MT) comprising nucleotides complementary to the mutant as template, can be used as a starting point for complementary strand synthesis when the specific nucleotide was a mutant.

For example, if the $82^{nd}$ nucleotide of SEQ ID NO: 50 was T instead of A, the MT primer sequence was designed so as to initiate the expected amplification reaction. Also, the WT primer comprises nucleotides complementary to the wild-type nucleotides. Therefore, when it is utilized as a template to synthesize a complementary strand, the 3' end can act as a starting point for complementary strand synthesis for a wild-type nucleotide. That is, the WT primer can be referred to as a SNP recognition primer.

As template, a 106-mer polynucleotide comprising a λDNA-derived nucleotide sequence designated as SEQ ID NO: 50 was used. The reaction conditions were as follows:

| Reaction composition (in 25 μL) | |
|---|---|
| 20 mM | Tris-HCl pH 8.8 |
| 10 mM | KCl |
| 10 mM | $(NH_4)_2SO_4$ |
| 4 mM | $MgSO_4$ |
| 0.8 M | Betaine |
| 0.1% | Triton X-100 |
| 0.4 mM | dNTP |
| 8 U | Bst DNA Polymerase (NEW ENGLAND BioLabs) |
| 0.25 μg/ml | EtBr |
| Primers: | |
| 800 nM Inner F | 400 nM Loop F |
| 800 nM Inner R | 400 nM Loop R |
| 200 nM Outer F | |
| 200 nM Outer R | |

Template DNA and each primer sequence used in the experiment are described below:

```
λDNA 3
5'-GCTCACTGTTCAGGCCGGAGCCACAGACCGCCGTTGAATGGGCGGATGCTAATTACTATCTCC    (SEQ ID NO:50)

CGAAAGAATCCGCATACCAGGAAGGGCGCTGGGAAACACTGCCCTTTCAGCGGGCCATCATGA

ATGCGATGGGCAGCGACTACATCCG-3'

InnerF_WT
TGGTATGCGGATTCTTTCGGGAGGCTCACTGTTCAGGCCGGAG                          (SEQ ID NO:51)

InnerR_WT
AGGAAGGGCGCTGGGAAACACTCGGATGTAGTCGCTGCCCATC                          (SEQ ID NO:52)

InnerF_MT
AGGTATGCGGATTCTTTCGGGAGGCTCACTGTTCAGGCCGGAG                          (SEQ ID NO:53)

InnerR_MT
TGGAAGGGCGCTGGGAAACACTGGGATGTAGTCGCTGCCCATC                          (SEQ ID NO:54)

OuterF
AACAGGCTGCGGCATTTTGTC                                                (SEQ ID NO:55)

OuterR
GGCAGACTTCACCACATTCACCTC                                             (SEQ ID NO:56)

LoopF
GAGATAGTAATTAGCATCCGCC                                               (SEQ ID NO:57)

LoopR
CACTGCCCTTTCAGCGGGCCAT                                               (SEQ ID NO:58)

LoopF_WT
TGGTATGCGGATTCTTTCGGGAGGAGATAGTAATTAGCATCCGCC                        (SEQ ID NO:59)

LoopR_WT
AGGAAGGGCGCTGGGAAACACTCACTGCCCTTTCAGCGGGCCAT                         (SEQ ID NO:60)
```

```
LoopF_MT
AGGTATGCGGATTCTTTCGGGAGGAGATAGTAATTAGCATCCGCC                    (SEQ ID NO:61)

LoopR_MT
TGGAAGGGCGCTGGGAAACACTCACTGCCCTTTCAGCGGGCCAT                     (SEQ ID NO:62)
```

A Non-heat denatured template polynucleotide (λDNA, $10^6$ molecules) was prepared. The reaction was carried out at 66° C. and using ABI PRISM 7700 (Perkin-Elmer Biosystems), to periodically observe the transition of the amplification.

Figure 15:
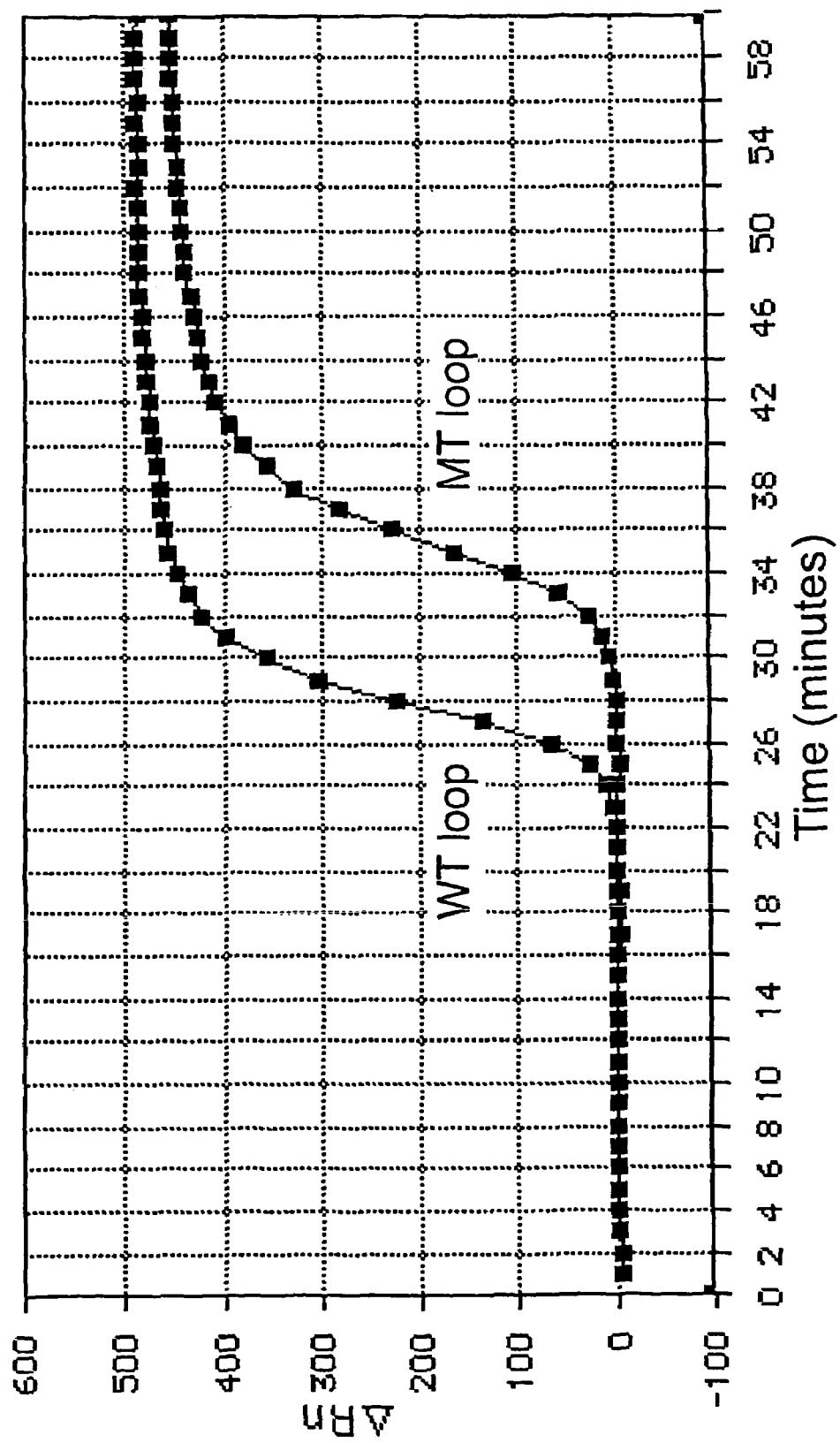
FIG. 15 shows the evaluation of SNP recognition at the 5' end of a loop primer. The X-axis indicates the reaction time and the Y-axis indicates the fluorescence intensity (ΔRn).
Figure 16:
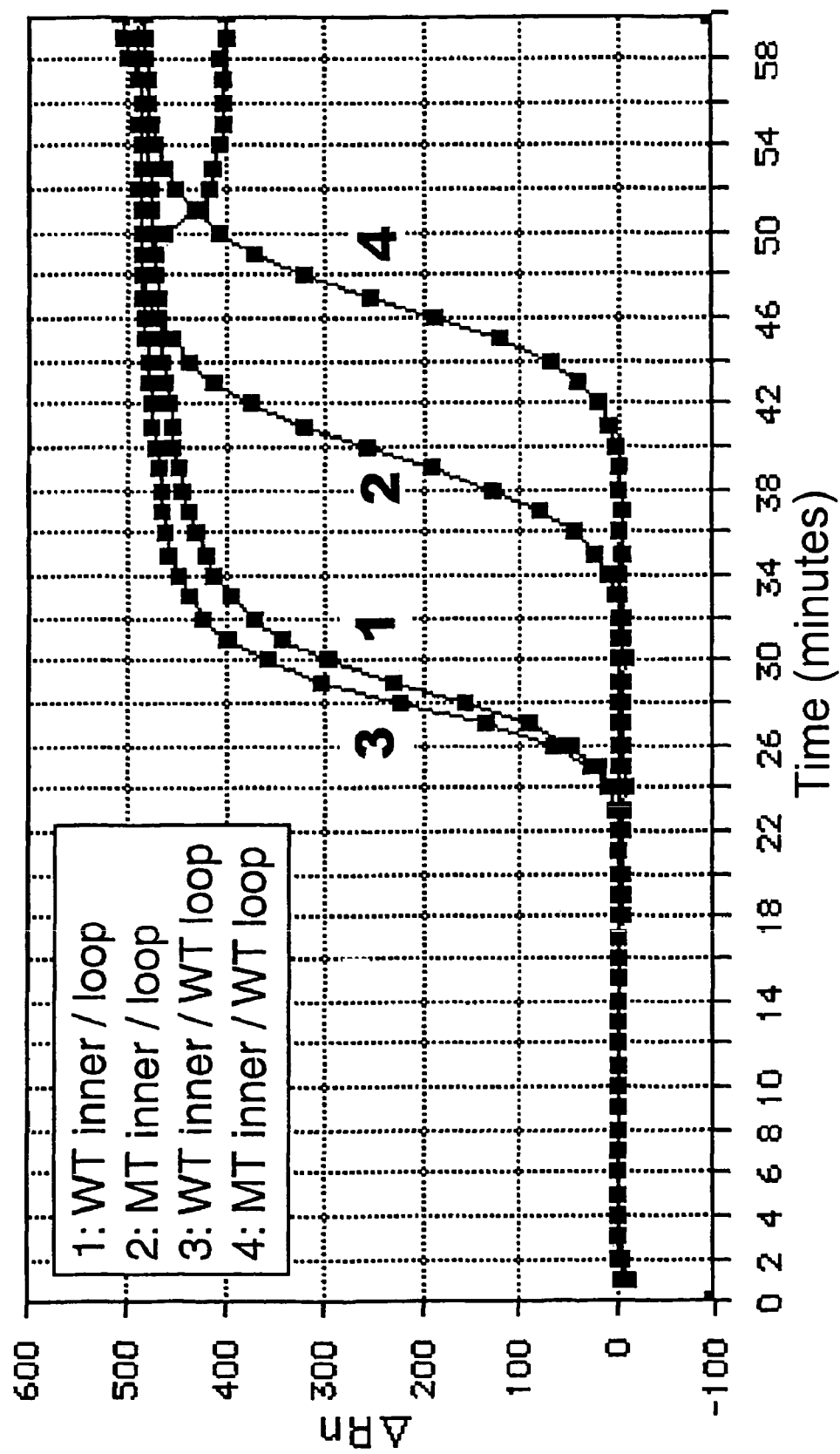
FIG. 16 shows the evaluation of the SNP recognition at the 5' end of an inner primer and loop primer. The X-axis indicates the reaction time and the Y-axis indicates the change in fluorescence intensity (ΔRn).

The result of the reaction is shown in FIGS. 15 and 16. First, the loop primers with the F1 (or R1) region added to the 5' side were used to examine if their 5' ends were able to detect SNPs (FIG. 15). For the inner primer, a sequence that recognizes an SNP (WT) was used. The result demonstrated that the increase in the signal when using a loop primer (MT loop) that cannot recognize an SNP at the 5' end was slower compared to that when using a primer that can recognize the SNP (WT loop). That is, this indicated that by changing the 5' end of the above primers to different nucleotides, an SNP could be detected based on the difference in the reaction rate.

Next, the LAMP reaction was carried out using inner primers that recognize SNPs. Similar to Example 1, the inventor used loop primers, in particular those with no additional specific sequences at their 5' sides, and only nucleotide sequences at the 5' sides were changed. The result demonstrated that even when combining with a loop primer, as described in the WO 01/34838 by the present applicant, utilization of the nucleotide sequences located at the 5' side of inner primers enabled the detection of a one-nucleotide difference (FIGS. 16-1 and 2).

In order to make the difference between FIGS. 16-1 and 2 larger, the above-mentioned loop primer (WT loop) was used to conduct the LAMP reaction. Consequently, as shown in FIG. 16-4, the signal increased much slower than in FIG. 16-2. The difference in reaction rates between wild type and mutant could be clearly identified by using a loop primer with a nucleotide sequence added to the 5' side, compared to when using only the inner primer.

When a mutant is detected based on the LAMP method, a smaller difference in signals can be seen between the wild type and mutant forms. One of the mechanisms behind this reduction of signal difference is thought to be as follows. For instance, when the wild type is used as a template, it is assumed that the reaction proceeds using the inner primer (Mt inner) for detecting a mutation. When, this reaction product functions as a template, the MT inner primer anneals to a portion produced using the primer sequence as template, and complementary strand synthesis is initiated. As a result, a nucleotide substitution occurs at the SNP position that should have been recognized, and the mutated template is amplified.

Figure 17:
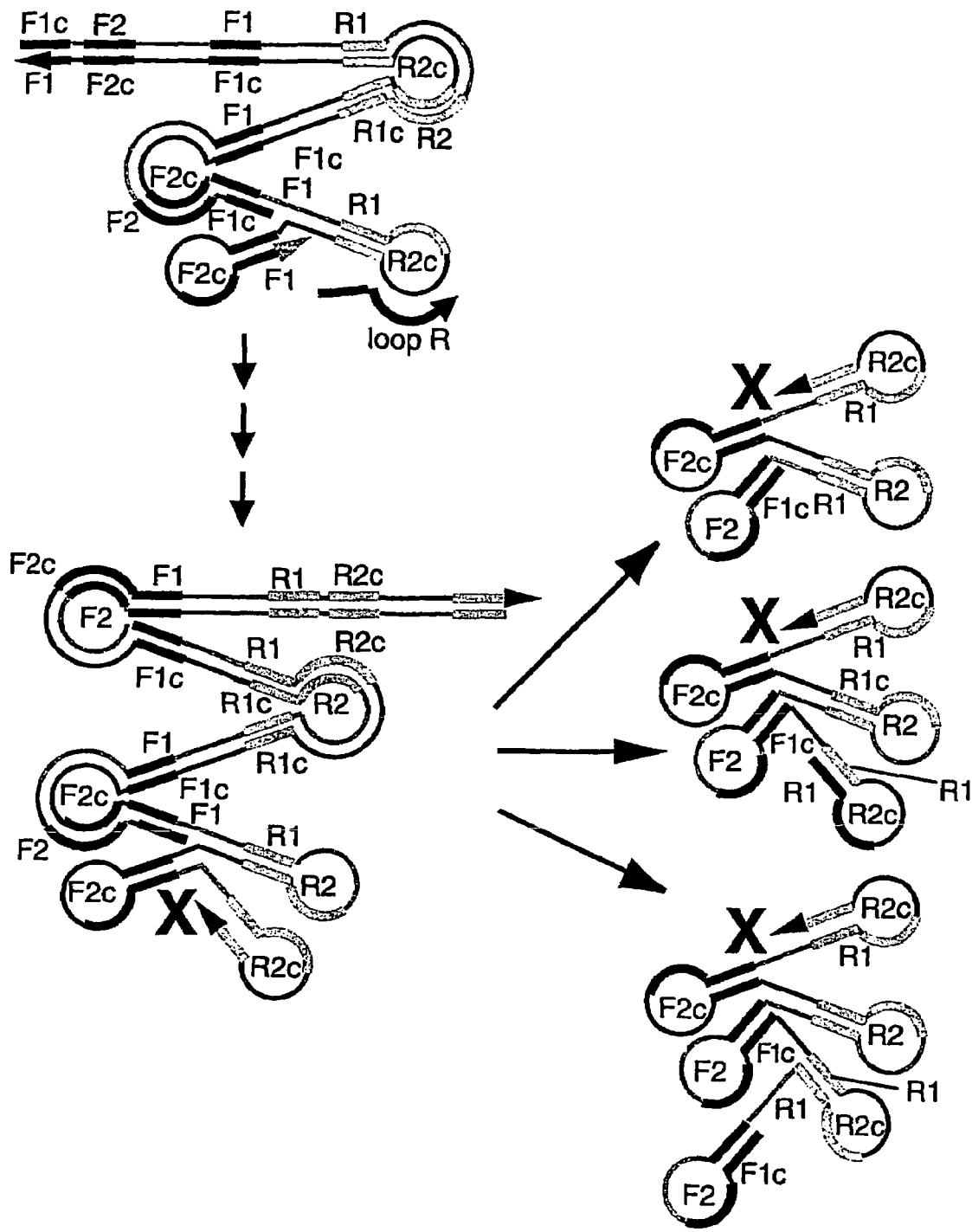
FIG. 17 illustrates the reaction principle of the SNP detection method used in the present invention.

In this example, a mechanism to check for a nucleotide substitution in the template was accomplished by using a loop primer capable of checking a specific nucleotide sequence at the 5' side. The principal of this checking mechanism is shown in FIG. 17. Using this method, an unfavorable amplification reaction is repressed based on the mechanism as described above, resulting in a clear difference in signal as shown in FIG. 16-4.

INDUSTRIAL APPLICABILITY

The present invention provides a rapid polynucleotide synthesis method. The polynucleotide synthesis method of the present invention can be conducted by using template polynucleotides that can form loop structures, and a plurality of primers that can bind to the loops to initiate complementary strand synthesis. A template polynucleotide that forms a loop structure can be synthesized easily by known methods such as the LAMP method. By the application of the LAMP method, all reactions involved can be performed at the same temperature. Therefore, in the present invention, by applying the LAMP method, all of the reactions can be done at the same temperature. Moreover, the present invention maintains high specificity and a large amount of polynucleotides can be produced in a short time.

Theoretically, the LAMP method rarely produces non-specific products. When the present invention is applied to the LAMP method, a loop primer can be designed in such a way that that it anneals to a specific reaction product. In this case, polynucleotides are synthesized rapidly only when appropriate reaction products are produced. Applying the present invention to the LAMP method makes it more difficult for non-specific reactions to occur. Thus, the present invention enables improvement of not only reaction efficiency, but also reaction specificity of the LAMP method.

The method of the present invention can be conducted simply by adding at least one loop primer to the primers necessary for the LAMP method. Therefore, the method of the present invention can be referred to as a flexible method with a potential for wide use. A reagent for practicing the present invention can be prepared by just adding a loop primer to the reagents for the LAMP method. Thus, a reagent kit can be easily produced.

The LAMP method is a polynucleotide amplification method that is highly specific and easy to operate. The present invention provides all the advantages of the LAMP method, and moreover, greatly increases the complementary strand synthesis reaction rate.

There is a growing need for analyzing SNPs and gene function, as well as gene diagnosis based on the results of those analyses. Thus, the development of a technology that enables gene nucleotide sequences to be analyzed more accurately and rapidly is becoming an important issue, not only in terms of rapidly carrying out functional analysis, but also with respect to practical application of the results of gene function analysis in actual clinical settings.

In fact, clinical trials of pharmaceutical agents developed based on SNP analyses have already commenced. When using such pharmaceutical agents that have passed the clinical trials, a method for simple and rapid SNP analysis of patient genomes at hospital bedsides will be essential. The present invention accomplished a useful gene analysis technique that can meet such a high need.

The invention claimed is:

1. A method for synthesizing a polynucleotide comprising the steps of mixing the following elements 1 to 5, and incubating under conditions that allow template-dependent complementary strand synthesis using the DNA polymerase in 4:
   1: a template polynucleotide that:
      (a) has a target nucleotide sequence comprising at least one set of complementary nucleotide sequences,
      (b) forms a loop capable of base pairing when the complementary nucleotide sequence of (a) hybridizes,
      (c) forms a loop by the annealing of its 3'-end to itself, and
      (d) whose 3'-end annealed to itself can be a starting point for complementary strand synthesis using itself as template;
   2: at least two types of primers providing staffing points for complementary strand synthesis at different locations on the template polynucleotide loop;
   3: at least one type of primer providing a staffing point for complementary strand synthesis at a location different from the primers of 2 in a loop formed by the template polynucleotide and/or an elongation product produced by the annealing of the primers of 2 to the template polynucleotide;
   4: a DNA polymerase catalyzing complementary strand synthesis accompanying strand displacement; and,
   5: a substrate for complementary strand synthesis.

2. The method of claim 1, wherein said template polynucleotide has on its 5'-end a nucleotide sequence complementary to an arbitrary region of its own nucleotide sequence.

3. The method of claim 2, wherein said template polynucleotide is produced by the following steps of:
   a) annealing a first primer to a target nucleotide sequence, and conducting a complementary strand synthesis reaction using this as a starting point, wherein said first primer (i) can provide at the 3'-end a starting point for complementary strand synthesis to a region that defines the 3'-side of one of the strands that compose the target nucleotide sequence, and (ii) has on its 5'-side a nucleotide sequence complementary to an arbitrary region of a complementary strand synthesis reaction product that uses this primer as a starting point;
   b) placing, in a condition that allows base pairing, the region to where a second primer is to anneal in the elongation product of the first primer synthesized in step a), wherein said second primer (i) has on its 3'-end a nucleotide sequence providing a staffing point for complementary strand synthesis to a region that defines the 3'-side of a target nucleotide sequence in the elongation product that uses the first primer as a staffing point, and (ii) has on its 5'-side a nucleotide sequence that is complementary to an arbitrary region of a complementary strand synthesis reaction product that uses this primer as an starting point;
   c) annealing said second primer to the region that can form base pairing in step b), and carrying out complementary strand synthesis using this as a starting point; and,
   d) annealing the 3'-end of the elongation product of the second primer synthesized in step c) to itself, and carrying out complementary strand synthesis using itself as template.

4. The method of claim 3, wherein the two types of primers are a first primer and a second primer, and at least one type of the primers is a loop primer providing, between a region derived from each primer in the elongation product of the first primer or second primer and the arbitrary region with respect to each primer, a starting point for complementary strand synthesis.

5. The method of claim 4, wherein said loop primer is (i) a first loop primer providing, between a region derived from the first primer in the elongation product of the first primer and the arbitrary region with respect to the first primer, a starting point for complementary strand synthesis, and (ii) a second loop primer providing, between a region derived from the second primer in the elongation product of the second primer and the arbitrary region with respect to the second primer, a staffing point for complementary strand synthesis.

6. The method of claim 4, wherein said loop primer further comprises on its 5'-end a nucleotide sequence complementary to the arbitrary region.

7. The method of claim 3, wherein each product of the first primer or second primer is converted to a single strand by displacing the elongation product of the first primer and/or second primer according to complementary strand synthesis from an outer primer that provides a starting point for complementary strand synthesis to the 3'-side of a template with respect to the first primer or second primer in step b) and/or step c).

8. The method of claim 3, wherein the target nucleotide sequence is present as a double-stranded polynucleotide in step a), and the region to which the first primer is annealed is made to form base pair bonds according to a complementary strand synthesis reaction using the arbitrary primer as a starting point.

9. The method of claim 8, wherein step a) is carried out in the presence of a melting temperature regulator.

10. The method of claim 9, wherein the melting temperature regulator is at least one compound selected from the group consisting of betaine, proline, dimethylsulfoxide, and trimethylamine N-oxide.

11. A method for amplifying a template polynucleotide, comprising the step of repeating complementary strand synthesis using the template polynucleotide as template according to the method of claim 1, and also carrying out another polynucleotide synthesis reaction according to the method of claim 1 using the elongation product resulting from the synthesis reaction as a new template polynucleotide.

12. A method for detecting a target nucleotide sequence in a sample, comprising the step of carrying out the amplification method of claim 11, and correlating the production of the amplification reaction product with the presence of a target nucleotide sequence.

13. The method of claim 12, wherein the method of claim 11 is carried out in the presence of a polynucleotide detecting agent, and whether or not an amplification reaction product is produced is observed based on a signal change of the detecting agent.

14. A method for detecting a mutation in a target nucleotide sequence according to the detection method of claim 12, the method comprising the steps of (i) blocking at least one of the complementary strand synthesis reactions selected from the complementary strand synthesis reactions composing the amplification method, when the target nucleotide sequence is not the predicted nucleotide sequence, and (ii) observing the inhibition of the amplification reaction.

15. The method of claim 14 that uses the following first primer and second primer, wherein at least either the first primer or second primer comprises a checking sequence on its 5'-side, wherein, a checking sequence refers to a nucleotide sequence in which (i) when a nucleotide sequence that composes a specific region is not the predicted nucleotide sequence, a mismatch occurs at the time when the 3'-end of the complementary strand synthesized using the checking sequence as template anneals to the target nucleotide sequence, or its complementary strand, and (ii) a complementary strand synthesis reaction that starts by using the 3'-end as a starting point is inhibited by this mismatch, the first primer (i) can provide at its 3'-end a starting point for complementary strand synthesis to a region that defines the 3'-side of one of the strands that composes a target nucleotide sequence, and (ii) has on its 5'-side a nucleotide sequence that is complementary to the arbitrary region of the complementary strand synthesis reaction product that uses this primer as a starting point, and the second primer (i) has a nucleotide sequence on its 3'-end that provides a staffing point for complementary strand synthesis to a region that defines the 3'-side of a target nucleotide sequence in an elongation product that uses the first primer as a starting point, and (ii) has on its 5'-side a nucleotide sequence that is complementary to the arbitrary region of the complementary strand synthesis reaction product that uses this primer as a staffing point.

16. The method of claim 15, wherein when the nucleotide sequence that composes the specific region is not the predicted nucleotide sequence, a mismatch occurs in the 2nd to 4th nucleotides from the 3'-end of the complementary strand at the time when the complementary strand synthesized by using a checking sequence as template anneals to the target nucleotide sequence, or its complementary strand.

17. The method of claim 15 that uses the following first loop primer and/or second loop primer as loop primers; provided that, when the loop primer comprises on its 5'-side a nucleotide that is complementary to the arbitrary region arranged on the 5'-side of the primer, or when the nucleotide sequence arranged on the 5'-side of the primer is a checking sequence, a sequence in which the nucleotide for providing the mismatch in the checking sequence differs from the checking sequence is arranged on the 5'-side of the loop primer:

first loop primer: provides, between a region derived from a first primer in an elongation product of the first primer and the arbitrary region with respect to the first primer, a staffing point for complementary strand synthesis;

second loop primer: provides, between a region derived from a second primer in an elongation product of the second primer and the arbitrary region with respect to the second primer, a staffing point for complementary strand synthesis.

18. The method of claim 17, wherein, when the nucleotide sequence that composes the specific region is not the predicted nucleotide sequence, a mismatch occurs in the 2nd to 4th nucleotides from the 3'-end of the complementary strand at the time when the complementary strand synthesized using a checking sequence as a template anneals to the target nucleotide sequence, or its complementary strand, and wherein, the nucleotide sequence arranged on the 5'-side of the first loop primer and/or second loop primer differs in the nucleotide that causes the mismatch in the checking sequence.

* * * * *

UNITED STATES PATENT AND TRADEMARK OFFICE
CERTIFICATE OF CORRECTION

PATENT NO. : 7,374,913 B2  Page 1 of 1
APPLICATION NO. : 10/380930
DATED : May 20, 2008
INVENTOR(S) : Kentaro Nagamine It is certified that error appears in the above-identified patent and that said Letters Patent is hereby corrected as shown below:

In Claim 1, at Col. 67, line 52, delete "staffing" and insert --starting--; and
at Col. 67, line 55, delete "staffing" and insert --starting--.
In Claim 3, at Col. 68, line 52, delete "staffing" and insert --starting--; and
at Col. 68, line 55, delete "staffing" and insert --starting--.
In Claim 5, at Col. 69, line 16, delete "staffing" and insert --starting--.
In Claim 15, at Col. 70, line 20, delete "staffing" and insert --starting--; and
at Col. 70, line 27, delete "staffing" and insert --starting--.
In Claim 17, at Col. 70, line 48, delete "staffing" and insert --starting--; and
at Col. 70, line 52, delete "staffing" and insert --starting--.

Signed and Sealed this

Twelfth Day of October, 2010

David J. Kappos
*Director of the United States Patent and Trademark Office*

SEQUENCE LISTING

<160> NUMBER OF SEQ ID NOS: 62

<210> SEQ ID NO 1
<211> LENGTH: 245
<212> TYPE: DNA
<213> ORGANISM: Bacteriophage lambda

<400> SEQUENCE: 1
ggcttggctc tgctaacacg ttgctcatag gagatatggt agagccgcag acacgtcgta    60
tgcaggaacg tgctgcggct ggctggtgaa cttccgatag tgcgggtgtt gaatgatttc   120
cagttgctac cgattttaca tattttttgc atgagagaat ttgtaccacc tcccaccgac   180
catctatgac tgtacgccac tgtccctagg actgctatgt gccggagcgg acattacaaa   240
cgtcc                                                              245

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 2
cagccagccg cagcacgttc gctcatagga gatatggtag agccgc                  46

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3
gagagaattt gtaccacctc ccaccgggca catagcagtc ctagggacag t             51

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4
ggcttggctc tgctaacacg tt                                             22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5
ggacgtttgt aatgtccgct cc                                             22

<210> SEQ ID NO 6
<211> LENGTH: 17
<212> TYPE: DNA
<213> ORGANISM: Artificial Sequence

```
<220> FEATURE:
<223> OTHER INFORMATION: Description of Artificial Sequence:an
      artificially synthesized primer sequence

<400> SEQUENCE: 6
ctgcatacga cgtgtct                                                        17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
agacacgtcg tatgcag                                                        17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 8
accatctatg actgtacgcc                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9
ggcgtacagt catagatggt                                                     20

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
tgcatacgac gtgtct                                                         16

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
gcatacgacg tgtct                                                          15

<210> SEQ ID NO 12
<211> LENGTH: 19
<212> TYPE: DNA
<213> ORGANISM: Artificial Sequence
<220> FEATURE:
```

```
<223> OTHER INFORMATION: Description of Artificial Sequence:an
      artificially synthesized primer sequence

<400> SEQUENCE: 12
ccatctatga ctgtacgcc                                                    19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
catctatgac tgtacgcc                                                     18

<210> SEQ ID NO 14
<211> LENGTH: 351
<212> TYPE: DNA
<213> ORGANISM: Bacteriophage lambda

<400> SEQUENCE: 14
cctgcctcca aacgatacct gttagcaata tttaatagct tgaaatgatg aagagctctg        60
tgtttgtctt cctgcctcca gttcgccggg cattcaacat aaaaactgat agcacccgga      120
gttccggaaa cgaaatttgc atataccat tgctcacgaa aaaaaatgtc cttgtcgata       180
tagggatgaa tcgcttggtg tacctcatct actgcgaaaa cttgaccttt ctctcccata      240
ttgcagtcgc ggcacgatgg aactaaatta ataggcatca ccgaaaattc aggataatgt      300
gcaataggaa gaaatgatc tatatttttt gtctgtccta tatcaccaca a                351

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 15
cgtgagcaat gggtatatgc aaatagagct ctgtgtttgt cttcctgc                    48

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16
atgtccttgt cgatataggg atgaagcaca ttatcctgaa ttttcggtg                   49

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 17
cctgcctcca aacgatacct                                                   20
```

```
<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 18
ttgtggtgat ataggacaga ca                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 19
ggaactccgg gtgctatcag                                                 20

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 20
tgacctttct ctcccatatt gcagtcg                                         27

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 21
ccggcgaact ggaggca                                                    17

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 22
cgatggaact aaattaatag gcatcac                                         27

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 23
aatttcgttt ccggaactcc                                                 20
```

```
<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 24
gaatcgcttg gtgtacctca tctactg                                        27

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 25
atatgcaaat tcgtttccg gaact                                           25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 26
tagggatgaa tcgcttggtg tacct                                          25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 27
cgtgagcaat gggtatatgc aaat                                           24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 28
atgtccttgt cgatataggg atgaa                                          25

<210> SEQ ID NO 29
<211> LENGTH: 264
<212> TYPE: DNA
<213> ORGANISM: Homo sapiens

<400> SEQUENCE: 29
ctggtagaag tgagttttgg atagtaaaat aagtttcgaa ctctggcacc tttcaatttt    60
gtcgcactct ccttgttttt gacaatgcaa tcatatgctt ctgctatgtt aagcgtattc   120
aacagcgatg attacagtcc agctgtgcaa gagaatattc ccgctctccg gagaagctct   180
tccttccttt gcactgaaag ctgtaactct aagtatcagt gtgaaacggg agaaaacagt   240
```
aaaggcaacg tccaggatag agtg                                          264

<210> SEQ ID NO 30
<211> LENGTH: 57
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 30
gcatatgatt gcattgtcaa aaacaaggag aataagtttc gaactctggc acctttc      57

<210> SEQ ID NO 31
<211> LENGTH: 55
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 31
gagaagctct tccttccttt gcactgaatt tactgttttc tcccgtttca cactg        55

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 32
ctggtagaag tgagttttgg atagt                                          25

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 33
cactctatcc tggacgttgc c                                              21

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 34
agtgcgacaa aatt                                                      14

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 35
agctgtaact ctaagtat                                                     18

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 36
cgtgagcaat gggtatatgc aaatggaact ccgggtgcta tcag                         44

<210> SEQ ID NO 37
<211> LENGTH: 52
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 37
atgtccttgt cgatataggg atgaatgacc tttctctccc atattgcagt cg               52

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 38
ttcgtttccg gaactccggg ttgaatgccc ggcgaactgg ag                           42

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 39
tcgcttggtg tacctcatct actgcggcag tcgcggcacg atggaacta                   49

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 40
ttcgtttccg gaactccggg tctccagttc gccgggcatt ca                           42

<210> SEQ ID NO 41
<211> LENGTH: 49
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 41
tcgcttggtg tacctcatct actgcgtagt tccatcgtgc cgcgactgc                   49

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 42
ctccagttcg ccgggcattc attcgtttcc ggaactccgg gt                42

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 43
tagttccatc gtgccgcgac tgctcgcttg gtgtacctca tctactgcg         49

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 44
tccagttcgc cgggcattgt ttccggaact ccgggt                      36

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 45
tagttccatc gtgccgcgac ttcgcttggt gtacctcatc tactg            45

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 46
atttgcatat acccattgct cacgggaact ccgggtgcta tcag             44

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence:an
    artificially synthesized primer sequence

<400> SEQUENCE: 47
ttcatcccta tatcgacaag gacattgacc tttctctccc atattgcagt cg    52

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 48
cgtgagcaat gggtatatgc aaatttcgtt tccggaactc cgggt         45

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 49
atgtccttgt cgatataggg atgaatcgct tggtgtacct catctactgc g         51

<210> SEQ ID NO 50
<211> LENGTH: 151
<212> TYPE: DNA
<213> ORGANISM: Bacteriophage lambda

<400> SEQUENCE: 50
gctcactgtt caggccggag ccacagaccg ccgttgaatg ggcggatgct aattactatc         60
tcccgaaaga atccgcatac caggaagggc gctgggaaac actgcccttt cagcgggcca        120
tcatgaatgc gatgggcagc gactacatcc g                                        151

<210> SEQ ID NO 51
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 51
tggtatgcgg attctttcgg gaggctcact gttcaggccg gag         43

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 52
aggaagggcg ctgggaaaca ctcggatgta gtcgctgccc atc         43

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 53
aggtatgcgg attctttcgg gaggctcact gttcaggccg gag         43

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 54
tggaagggcg ctgggaaaca ctcggatgta gtcgctgccc atc                43

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 55
aacaggctgc ggcattttgt c                                        21

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 56
ggcagacttc accacattca cctc                                     24

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 57
gagatagtaa ttagcatccg cc                                       22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 58
cactgccctt tcagcgggcc at                                       22

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 59
tggtatgcgg attctttcgg gaggagatag taattagcat ccgcc              45

-continued

```
<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 60
aggaagggcg ctgggaaaca ctcactgccc tttcagcggg ccat                44

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 61
aggtatgcgg attctttcgg gaggagatag taattagcat ccgcc              45

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 62
tggaagggcg ctgggaaaca ctcactgccc tttcagcggg ccat                44
```